United States Patent
Chen et al.

(10) Patent No.: US 8,592,594 B2
(45) Date of Patent: *Nov. 26, 2013

(54) TETRAHYDRO-QUINOLINE DERIVATIVES

(75) Inventors: Li Chen, Shanghai (CN); Lichun Feng, Shanghai (CN); Yun He, Shanghai (CN); Mengwei Huang, Shanghai (CN); Yongfu Liu, Shanghai (CN); Hongying Yun, Shanghai (CN); Mingwei Zhou, Shanghai (CN)

(73) Assignee: Hoffmann-La Roche Inc., Nutley, NJ (US)

( * ) Notice: Subject to any disclaimer, the term of this patent is extended or adjusted under 35 U.S.C. 154(b) by 170 days.

This patent is subject to a terminal disclaimer.

(21) Appl. No.: 13/169,097

(22) Filed: Jun. 27, 2011

(65) Prior Publication Data
US 2012/0004218 A1    Jan. 5, 2012

(30) Foreign Application Priority Data
Jul. 2, 2010  (WO) ................ PCT/CN2010/074931

(51) Int. Cl.
*C07D 215/38*  (2006.01)

(52) U.S. Cl.
USPC ......................................... 546/165; 546/122

(58) Field of Classification Search
USPC ................................ 546/165, 122
See application file for complete search history.

(56) References Cited

U.S. PATENT DOCUMENTS 8,344,137 B2 * 1/2013 Chen et al. ................... 544/128

FOREIGN PATENT DOCUMENTS

| EP | 0538477 | 4/1993 |
|---|---|---|
| WO | 2004/080971 | 9/2004 |

OTHER PUBLICATIONS

Carling, D., "Trends in Biochem. Science" 29:18-24 ( 2004).
Shaw et al., "Science New York, NY" 310:1642-1646 ( 2005).
Kadowaki et al., "The Journal of Clinical Investigation" 116:1784-1792 ( 2006).
Yamauchi et al., "Nature Medicine" 8:1288-1295 ( 2002).
Yamauchi et al., "Nature Medicine" 7:941-946 ( 2001).
Muoio et al., "Diabetes" 46:1360-1363 ( 1997).
Owen et al., "The Biochemical Journal" 348:607-614 ( 2000).
Friedman et al., "Nature" 395:763-770 ( 1998).
Zhou et al., "The Journal of Clinical Investigation" 108:1167-1174 ( 2001).
Kahn et al., "Cell Metabolism" 1:15-25 ( 2005).
Cool et al., "Cell Metabolism" 3:403-416 ( 2006).
Woods et al., "Molecular & Cellular Biology" 20:6704-6711 ( 2000).
Hardie et al., "Nature Reviews" 8:774-785 ( 2007).
Bastin et al., "Organic Process Research & Development" 4:427-435 ( 2000).
Pang et al., "The Journal of Biological Chemistry" 283:16051-16060 ( 2008).
El-Mir et al., "The Journal of Biological Chemistry" 275:223-228 ( 2000).
Semple et al., "The Journal of Clinical Investigation" 116:581-589 ( 2006).
Fryer et al., "The Journal of Biological Chemistry" 277:25226-25232 ( 2002).
Hardie, D. G., "Annual Review of Pharmacology & Toxicology" 47:185-210 ( 2007).
Long et al., "The Journal of Clinical Investigation" 116:1776-1783 ( 2006).
Ansel et al., "Pharm. Dosage Forms & Drug Delivery Systems":456-457 ( 1995).
Minokoshi et al., "Nature" 415:339-343 ( 2002).
(*International Search Report* in PCT/EP2011/060864 Sep. 28, 2011).

* cited by examiner

*Primary Examiner* — D M Seaman

(57) ABSTRACT

A compound of formula (I)

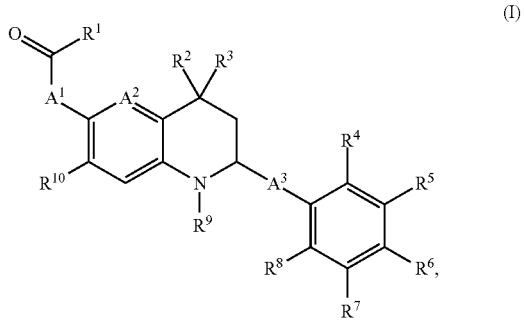

or a pharmaceutically acceptable salt or ester thereof, wherein $A^1$ to $A^3$ and $R^1$ to $R^{10}$ have the significance given in claim 1, can be used as a medicament. These compounds are useful in the treatment or prophylaxis of diseases that are related to AMPK regulation, such as obesity, dyslipidemia, hyperglycemia, type 1 or type 2 diabetes and cancers.

17 Claims, No Drawings

TETRAHYDRO-QUINOLINE DERIVATIVES

PRIORITY TO RELATED APPLICATION(S)

This application claims the benefit of PCT/CN2010/074931, filed Jul. 2, 2010, which is hereby incorporated by reference in its entirety.

FIELD OF THE INVENTION

The invention relates to compounds which are activators of AMP-activated protein kinase (AMPK) and which are useful in the treatment or prophylaxis of diseases that are related to AMPK regulation, such as obesity, dyslipidemia, hyperglycemia, type 1 or type 2 diabetes and cancers.

BACKGROUND OF THE INVENTION

Obesity and type 2 diabetes, hypertension and cardiovascular disease are diseases that feature serious disturbances in glucose or lipid metabolism that severely affect the health and quality of life of affected individuals. In addition, cancer metabolism is known to be different from normal cellular metabolism. The increasing prevalence of these diseases makes finding new drug targets for treating these syndromes an urgent task.

AMP-activated protein kinase acts as a cellular energy sensor and regulator. It is activated by an increase in the cellular AMP:ATP ratio induced by metabolic stress, hormone and nutrient signals and other cellular mechanisms such as phosphorylation and protein-protein interaction. Once activated, AMPK switches on catabolic pathways that generate ATP and switches off ATP-consuming anabolic pathways by acute regulation of the activity of key enzymes in metabolism and chronic regulation of the expression of pivotal transcription factors (Hardie, D G. *Nature reviews* 8 (2007b), 774-785; Woods, A et al. *Molecular and cellular biology* 20 (2000), 6704-6711). The growing evidence of AMPK regulatory effects on glucose and lipid metabolism makes it a potential drug target for treatment of diabetes, metabolic syndrome and cancer (Carling, D. *Trends Biochem Sci* 29 (2004), 18-24; Hardie, D G. *Annual review of pharmacology and toxicology* 47 (2007a), 185-210; Kahn, B B et al. *Cell metabolism* 1 (2005), 15-25; Long, Y C et al. *The Journal of clinical investigation* 116 (2006), 1776-1783).

At the physiological level, this concept has been supported by two adipokines, leptin and adiponectin, both of which exert excellent effects on glucose and lipid metabolism (Friedman, J M and Halaas, J L. *Nature* 395 (1998), 763-770; Muoio, D M et al. *Diabetes* 46 (1997), 1360-1363; Yamauchi, T et al. *Nature medicine* 7 (2001), 941-946). Recent studies suggest that leptin and adiponectin exert their antidiabetic effects by activating AMPK. Leptin stimulates muscle fatty acid oxidation by activating AMPK directly and through a hypothalamic-adrenergic pathway (Minokoshi, Y et al. *Nature* 415 (2002), 339-343). Adiponectin stimulates glucose uptake and fatty acid oxidation in vitro by activation of AMPK. Furthermore, it exerts its hypoglycemic effect by decreasing PEPCK and G6Pase expression, whereas the administration of dominant negative α1 adenovirus reverses the effect in vivo (Yamauchi, T et al. *Nature medicine* 8 (2002), 1288-1295).

At the pharmacological level, the concept of AMPK as a potential target for treating metabolic syndrome has been further supported by the discovery of two major classes of existing antidiabetic drugs: thiazolidinediones (rosiglitazone, troglitazone and pioglitazone) and biguanides (metformin and phenformin) activate AMPK in cultured cells and in vivo. Rosiglitazone is traditionally considered to be a PPARγ agonist and exerts its antidiabetic effects through differentiation of adipocytes (Semple, R K et al. *The Journal of clinical investigation* 116 (2006), 581-589). Recent findings indicate that AMPK may be involved in the antidiabetic effects of rosiglitazone (Brunmair, B et al. *The Journal of biological chemistry* 277 (2002), 25226-25232; Kadowaki, T et al. *The Journal of clinical investigation* 116 (2006), 1784-1792). In the case of metformin, an existing antidiabetic agent without a defined mechanism of action, recent studies demonstrate that it could activate AMPK in vitro and in vivo by inhibiting complex I (El-Mir, M Y et al. *The Journal of biological chemistry* 275 (2000), 223-228; Owen, M R et al. *The Biochemical journal* 348 Pt 3 (2000), 607-614; Zhou, G et al. *The Journal of clinical investigation* 108 (2001), 1167-1174), and the hypoglycemic effect could be blocked completely by knockout of its upstream kinase LKB1, confirming the key role of AMPK in mediating the antidiabetic effect of metformin (Shaw, R J et al. *Science* (New York) N.Y. 310 (2005), 1642-1646).

Most recently, Cool and coworkers have identified a small direct AMPK activator, A-769662, which exerts antidiabetic effects in vivo (Cool, B et al. *Cell metabolism* 3 (2006), 403-416). Li's laboratory has also identified a small AMPK activator, PT1, which activates the inactive forms of AMPK α2$_{398}$ and α1$_{394}$ with micromolar activity and exerts some cellular effects (Pang, T et al. *The Journal of biological chemistry* 283 (2008), 16051-16060).

It has been found that the compounds of the present invention are potent AMPK activators. The compounds of the invention are therefore useful in the treatment or prophylaxis of diseases that are related to AMPK regulation, such as obesity, dyslipidemia, hyperglycemia, type 1 or type 2 diabetes and cancers.

SUMMARY OF THE INVENTION

The invention relates in part to compounds of formula (I)

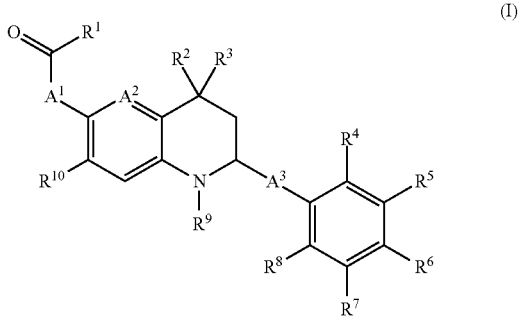

wherein
$A^1$ is absent or —CH$_2$—;
$A^2$ is nitrogen or —CH—;
$A^3$ is absent or —C(CH$_3$)$_2$—;
$R^1$ is hydroxyl or NR$^{11}$R$^{12}$;
$R^2$ and $R^3$ are each independently selected from the group consisting of alkyl, alkenyl and phenyl;
or $R^2$ and $R^3$ together with the carbon atom to which they are attached form cycloalkyl;
$R^4$, $R^5$, $R^6$, $R^7$ and $R^8$ are each independently selected from the group consisting of hydrogen, alkyl, alkoxy, halogen, alkylsulfonyl, morpholinyl, piperazinyl and alkylpiperazinyl;

$R^9$ is selected from the group consisting of hydrogen, alkyl, benzyl and alkylaminocarbonyl;

$R^{10}$ is hydrogen or halogen;

$R^{11}$ and $R^{12}$ are each independently selected from the group consisting of hydrogen, alkyl, cycloalkyl, hydroxyalkyl, oxetanyl, alkylpiperidinyl, 1,1-dioxothiomorpholinylalkyl and benzylpiperidinyl;

or $R^{11}$ and $R^{12}$ together with the nitrogen atom to which they are attached form morpholinyl, piperazinyl, alkylpiperazinyl, alkylsulfonylpiperazinyl, alkylhydroxypyrrolidinyl or hydroxyalkylpyrrolidinyl;

and pharmaceutically acceptable salts or esters thereof.

The invention also relates to a process for the manufacture of these novel compounds and medicaments containing them. The compounds of the invention have activation effect on AMP (adenosine monophosphate)-activated protein kinase, which results in lowered blood glucose and lipid levels. The invention thus also concerns the use of such compounds for the treatment or prophylaxis of diseases that are related to AMPK regulation, such as obesity, dyslipidemia, hyperglycemia, type 1 or type 2 diabetes, and cancers.

DETAILED DESCRIPTION OF THE INVENTION

As used herein, the term "alkyl", alone or in combination, signifies a saturated, linear or branched chain alkyl group containing 1 to 8, preferably 1 to 6, more preferably 1 to 4 carbon atoms, for example methyl, ethyl, propyl, isopropyl, 1-butyl, 2-butyl and tert-butyl. Preferred "alkyl" groups are methyl, ethyl, isopropyl and tert-butyl.

The term "alkenyl", alone or in combination, signifies an alkyl group as defined above wherein one or more carbon-carbon single bond is replaced by a carbon-carbon double bond. Examples of alkenyl are ethenyl, propenyl, n-butenyl and i-butenyl. Preferred alkenyl groups are ethenyl, propenyl and i-propenyl.

The term "alkoxy", alone or in combination, signifies a group alkyl-O—, wherein the "alkyl" is as defined above; for example methoxy, ethoxy, propoxy, isopropoxy, n-butoxy, i-butoxy, 2-butoxy and t-butoxy. Preferred alkoxy groups are methoxy and ethoxy and more preferably methoxy.

The term "cycloalkyl", alone or in combination, refers to a saturated carbon ring containing from 3 to 7 carbon atoms, preferably from 3 to 6 carbon atoms, for example, cyclopropyl, cyclobutyl, cyclopentyl, cyclohexyl, cycloheptyl and the like. Preferred cycloalkyl groups are cyclopropyl, cyclopentyl and cyclohexyl The term "halogen" means fluorine, chlorine, bromine or iodine. Halogen is preferably fluorine, chlorine or bromine.

The term "halophenyl" means phenyl substituted by halogen.

The term "carboxyl", alone or in combination, refers to the group —COOH.

The term "carbonyl", alone or in combination, refers to the group —C(O)—.

The term "amino", alone or in combination, refers to primary (—NH$_2$—), secondary (—NH—) or tertiary amino (—N—).

The term "hydroxy", alone or in combination, refers to the group —OH.

The term "sulfonyl", alone or in combination, refers to the group —S(O)$_2$—.

The compounds according to the present invention may exist in the form of their pharmaceutically acceptable salts. The term "pharmaceutically acceptable salt" refers to conventional acid-addition salts or base-addition salts that retain the biological effectiveness and properties of the compounds of formula (I) and are formed from suitable non-toxic organic or inorganic acids or organic or inorganic bases. Acid-addition salts include for example those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Base-addition salts include those derived from ammonium, potassium, sodium and, quaternary ammonium hydroxides, such as for example, tetramethyl ammonium hydroxide. The chemical modification of a pharmaceutical compound into a salt is a technique well known to pharmaceutical chemists in order to obtain improved physical and chemical stability, hygroscopicity, flowability and solubility of compounds. It is for example described in Bastin R. J., et. al. organic Process Research & Development 2000, 4, 427-435; or in Ansel, H., et. al., In: Pharmaceutical Dosage Forms and Drug Delivery Systems, 6th ed. (1995), pp. 196 and 1456-1457. Preferred are the sodium salts of the compounds of formula (I).

"Pharmaceutically acceptable esters" means that compounds of general formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compounds of general formula (I), similar to the metabolically labile esters, which are capable of producing the parent compounds of general formula (I) in vivo, are within the scope of this invention. Preferred are the methyl and ethyl esters of the compounds of formula (I).

The invention relates in part to compounds of formula (I)

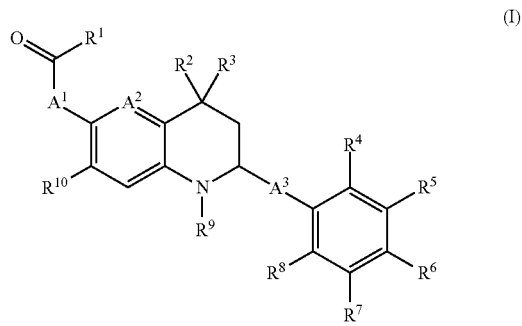

(I)

wherein $A^1$ is absent or —CH$_2$—;

$A^2$ is nitrogen or —CH—;

$A^3$ is absent or —C(CH$_3$)$_2$—;

$R^1$ is hydroxyl or $NR^{11}R^{12}$;

$R^2$ and $R^3$ are each independently selected from the group consisting of alkyl, alkenyl and phenyl;

or $R^2$ and $R^3$ together with the carbon atom to which they are attached form cycloalkyl;

$R^4$, $R^5$, $R^6$, $R^7$ and $R^8$ are each independently selected from the group consisting of hydrogen, alkyl, alkoxy, halogen, alkylsulfonyl, morpholinyl, piperazinyl and alkylpiperazinyl;

$R^9$ is selected from the group consisting of hydrogen, alkyl, benzyl and alkylaminocarbonyl;

$R^{10}$ is hydrogen or halogen;

R¹¹ and R¹² are each independently selected from the group consisting of hydrogen, alkyl, cycloalkyl, hydroxyalkyl, oxetanyl, alkylpiperidinyl, 1,1-dioxothiomorpholinylalkyl and benzylpiperidinyl;

or R¹¹ and R¹² together with the nitrogen atom to which they are attached form morpholinyl, piperazinyl, alkylpiperazinyl, alkylsulfonylpiperazinyl, alkylhydroxypyrrolidinyl or hydroxyalkylpyrrolidinyl;

and pharmaceutically acceptable salts or esters thereof.

In a particular embodiment of the invention, $A^1$ is absent. In another embodiment, $A^1$ is —CH$_2$—.

In another particular embodiment of the invention, $A^2$ is nitrogen. In a further embodiment of the invention, $A^2$ is —CH—.

Still in a particular embodiment of the invention, $A^3$ is absent. $A^3$ can also be —C(CH$_3$)$_3$—.

$R^1$ can be hydroxyl. In another particular embodiment of the invention, $R^1$ is NR$^{11}$NR$^{12}$.

In a particular embodiment of the invention, $R^2$ and $R^3$ are each independently selected from the group consisting of alkyl, alkenyl and phenyl.

In a particular embodiment of the invention, $R^2$ and $R^3$ together with the carbon atom to which they are attached form cycloalkyl.

In a particular embodiment of the invention, $R^2$ and $R^3$ are each independently selected from the group consisting of methyl, ethyl, ethenyl and phenyl, or $R^2$ and $R^3$ together with the carbon atom to which they are attached form cyclopropyl, cyclopentyl or cyclohexyl.

In a particular embodiment of the invention, $R^2$ and $R^3$ are each independently selected from the group consisting of methyl, ethyl, ethenyl and phenyl.

In a particular embodiment of the invention, $R^2$ and $R^3$ together with the carbon atom to which they are attached form cyclopropyl, cyclopentyl or cyclohexyl.

In a particular embodiment of the invention, $R^4$ is selected from the group consisting of hydrogen, alkyl, alkoxy, halogen and alkylsulfonyl.

In a particular embodiment of the invention, $R^4$ is selected from the group consisting of hydrogen, methyl, fluoro, chloro, bromo and methylsulfonyl.

In a particular embodiment of the invention, $R^5$ is selected from the group consisting of hydrogen, alkyl, alkoxy, halogen, alkylsulfonyl, morpholinyl, piperazinyl and alkylpiperazinyl.

In a particular embodiment of the invention, $R^5$ is selected from the group consisting of hydrogen, chloro, and morpholinyl.

In a particular embodiment of the invention, $R^6$ is hydrogen or halogen.

In a particular embodiment of the invention, $R^6$ is hydrogen or fluoro.

In a particular embodiment of the invention, $R^7$ is selected from the group consisting of hydrogen, halogen, alkylsulfonyl and morpholinyl.

In a particular embodiment of the invention, $R^7$ is selected from the group consisting of hydrogen, fluoro, chloro, bromo and methylsulfonyl.

In a particular embodiment of the invention, $R^8$ is hydrogen or alkyl.

In a particular embodiment of the invention, $R^8$ is hydrogen or methyl.

In a particular embodiment of the invention, $R^9$ is selected from the group consisting of hydrogen, pentyl, dimethylaminocarbonyl and benzyl.

In a particular embodiment of the invention, $R^{10}$ is hydrogen or chloro.

In a particular embodiment of the invention, $R^{11}$ and $R^{12}$ are each independently selected from the group consisting of hydrogen, alkyl, cycloalkyl, hydroxyalkyl and alkylpiperidinyl, or $R^{11}$ and $R^{12}$ together with the nitrogen atom to which they are attached form morpholinyl, piperazinyl, alkylpiperazinyl or alkylsulfonylpiperazinyl.

In a particular embodiment of the invention, $R^{11}$ and $R^{12}$ are each independently selected from the group consisting of hydrogen, alkyl, cycloalkyl, hydroxyalkyl and alkylpiperidinyl.

In a particular embodiment of the invention, $R^{11}$ and $R^{12}$ together with the nitrogen atom to which they are attached form morpholinyl, piperazinyl, alkylpiperazinyl or alkylsulfonylpiperazinyl.

In a particular embodiment of the invention, $R^{11}$ and $R^{12}$ are each independently selected from the group consisting of hydrogen, methyl, propyl, dihydroxybutyl, cyclopropyl, cyclobutyl, methylpiperidinyl and hydroxyethyl or $R^{11}$ and $R^{12}$ together with the nitrogen atom to which they are attached form morpholinyl, piperazinyl, methylpiperazinyl or methylsulfonylpiperazinyl.

In a particular embodiment of the invention, $R^{11}$ and $R^{12}$ are each independently selected from the group consisting of hydrogen, methyl, propyl, dihydroxybutyl, cyclopropyl, cyclobutyl, methylpiperidinyl and hydroxyethyl.

In a particular embodiment of the invention, $R^{11}$ and $R^{12}$ together with the nitrogen atom to which they are attached form morpholinyl, piperazinyl, methylpiperazinyl or methylsulfonylpiperazinyl.

In a particular embodiment of the invention, the compound can be selected from the group consisting of:

2-(5-Fluoro-2-methyl-phenyl)-spiro(cyclopropane-1,4'-1',2',3',4'-tetrahydroquinoline)-6-carboxylic acid;

2-(5-Bromo-2-fluoro-phenyl)-spiro(cyclopropane-1,4'-1',2',3',4'-tetrahydroquinoline)-6-carboxylic acid;

2-(2,5-Dichloro-phenyl)-spiro(cyclopropane-1,4'-1',2',3',4'-tetrahydroquinoline)-6-carboxylic acid;

2-(3,5-Dichloro-phenyl)-spiro(cyclopropane-1,4'-1',2',3',4'-tetrahydroquinoline)-6-carboxylic acid;

2-(5-Chloro-2-fluoro-phenyl)-spiro(cyclopropane-1,4'-1',2',3',4'-tetrahydroquinoline)-6-carboxylic acid;

2-(3-Methanesulfonyl-phenyl)-spiro(cyclopropane-1,4'-1',2',3',4'-tetrahydroquinoline)-6-carboxylic acid;

2-(2-Bromo-5-fluoro-phenyl)-spiro(cyclopropane-1,4'-1',2',3',4'-tetrahydroquinoline)-6-carboxylic acid;

2-(3-Fluoro-phenyl)-spiro(cyclopropane-1,4'-1',2',3',4'-tetrahydroquinoline)-6-carboxylic acid;

2-(2-Bromo-5-fluoro-phenyl)-spiro(cyclohexane-1,4'-1',2',3',4'-tetrahydroquinoline)-6-carboxylic acid;

2-(2-Bromo-5-fluoro-phenyl)-spiro(cyclopentane-1,4'-1',2',3',4'-tetrahydroquinoline)-6-carboxylic acid;

2-(5-Fluoro-2-methanesulfonyl-phenyl)-spiro(cyclopropane-1,4'-1',2',3',4'-tetrahydroquinoline)-6-carboxylic acid;

2-(2,5-Dimethanesulfonyl-phenyl)-spiro(cyclopropane-1,4'-1',2',3',4'-tetrahydroquinoline)-6-carboxylic acid;

2-(2,5-Dichloro-phenyl)-1-dimethylcarbamoyl-spiro(cyclopropane-1,4'-1',2',3',4'-tetrahydroquinoline)-6-carboxylic acid;

1-Benzyl-2-(2,5-dichloro-phenyl)-spiro(cyclopropane-1,4'-1',2',3',4'-tetrahydroquinoline)-6-carboxylic acid;

2-(2,5-Dichloro-phenyl)-4,4-dimethyl-1,2,3,4-tetrahydroquinoline-6-carboxylic acid;

4,4-Dimethyl-2-(1-methyl-1-phenyl-ethyl)-1,2,3,4-tetrahydro-quinoline-6-carboxylic acid;

7-Chloro-2-(5-chloro-2-fluoro-phenyl)-4,4-dimethyl-1,2,3,4-tetrahydro-quinoline-6-carboxylic acid;

[2-(5-Chloro-2-fluoro-phenyl)-4,4-dimethyl-1,2,3,4-tetrahydro-quinolin-6-yl]-acetic acid;
2-(3-Chloro-4-fluoro-phenyl)-4-methyl-4-vinyl-1,2,3,4-tetrahydro-quinoline-6-carboxylic acid;
2-(3-Chloro-4-fluoro-phenyl)-4-methyl-4-phenyl-1,2,3,4-tetrahydro-quinoline-6-carboxylic acid;
2-(5-Fluoro-2-isopropoxy-phenyl)-4,4-dimethyl-1,2,3,4-tetrahydro-quinoline-6-carboxylic acid;
4,4-Dimethyl-2-(3-morpholin-4-yl-phenyl)-1,2,3,4-tetrahydro-quinoline-6-carboxylic acid;
2-[3-(4-Isopropyl-piperazin-1-yl)-phenyl]-4,4-dimethyl-1,2,3,4-tetrahydro-quinoline-6-carboxylic acid;
4,4-Dimethyl-2-(3-piperazin-1-yl-phenyl)-1,2,3,4-tetrahydro-quinoline-6-carboxylic acid;
6-(3-Chloro-4-fluoro-phenyl)-8-methyl-8-vinyl-5,6,7,8-tetrahydro-[1,5]naphthyridine-2-carboxylic acid;
6-(3-Chloro-4-fluoro-phenyl)-8-ethyl-8-methyl-5,6,7,8-tetrahydro-[1,5]naphthyridine-2-carboxylic acid;
6-(3-Chloro-4-fluoro-phenyl)-8-ethyl-8-methyl-5-(3-methyl-butyl)-5,6,7,8-tetrahydro-[1,5]naphthyridine-2-carboxylic acid;
2-(5-Fluoro-2-methyl-phenyl)-spiro(cyclopropane-1,4'-1',2',3',4'-tetrahydroquinoline)-6-carboxylic acid cyclobutylamide;
2-(5-Fluoro-2-methyl-phenyl)-spiro(cyclopropane-1,4'-1',2',3',4'-tetrahydroquinoline)-6-carboxylic acid dimethylamide;
[2-(5-Fluoro-2-methyl-phenyl)-spiro(cyclopropane-1,4'-1',2',3',4'-tetrahydroquinolin)-6-yl]-morpholin-4-yl-methanone;
[2-(5-Fluoro-2-methyl-phenyl)-spiro(cyclopropane-1,4'-1',2',3',4'-tetrahydroquinolin)-6-yl]-(4-methyl-piperazin-1-yl)-methanone;
[2-(2-Bromo-5-fluoro-phenyl)-spiro(cyclopropane-1,4'-1',2',3',4'-tetrahydroquinolin)-6-yl]-morpholin-4-yl-methanone;
2-(2-Bromo-5-fluoro-phenyl)-spiro(cyclopropane-1,4'-1',2',3',4'-tetrahydroquinoline)-6-carboxylic acid isopropylamide;
2-(2-Bromo-5-fluoro-phenyl)-spiro(cyclopropane-1,4'-1',2',3',4'-tetrahydroquinoline)-6-carboxylic acid dimethylamide;
2-(2-Bromo-5-fluoro-phenyl)-spiro(cyclopropane-1,4'-1',2',3',4'-tetrahydroquinoline)-6-carboxylic acid cyclobutylamide;
2-(5-Bromo-2-fluoro-phenyl)-spiro(cyclopropane-1,4'-1',2',3',4'-tetrahydroquinoline)-6-carboxylic acid cyclobutylamide;
2-(2,5-Dichloro-phenyl)-spiro(cyclopropane-1,4'-1',2',3',4'-tetrahydroquinoline)-6-carboxylic acid cyclopropylamide;
2-(2,5-Dichloro-phenyl)-spiro(cyclopropane-1,4'-1',2',3',4'-tetrahydroquinoline)-6-carboxylic acid methylamide;
2-(2,5-Dichloro-phenyl)-spiro(cyclopropane-1,4'-1',2',3',4'-tetrahydroquinoline)-6-carboxylic acid cyclobutylamide;
[2-(2,5-Dichloro-phenyl)-spiro(cyclopropane-1,4'-1',2',3',4'-tetrahydroquinolin)-6-yl]-morpholin-4-yl-methanone;
2-(2,5-Dichloro-phenyl)-spiro(cyclopropane-1,4'-1',2',3',4'-tetrahydroquinoline)-6-carboxylic acid isopropylamide;
[2-(2,5-Dichloro-phenyl)-spiro(cyclopropane-1,4'-1',2',3',4'-tetrahydroquinolin)-6-yl]-(4-methanesulfonyl-piperazin-1-yl)-methanone;
2-(3,5-Dichloro-phenyl)-spiro(cyclopropane-1,4'-1',2',3',4'-tetrahydroquinoline)-6-carboxylic acid cyclobutylamide;
[2-(5-Chloro-2-fluoro-phenyl)-spiro(cyclopropane-1,4'-1',2',3',4'-tetrahydroquinolin)-6-yl]-morpholin-4-yl-methanone;
2-(5-Chloro-2-fluoro-phenyl)-spiro(cyclopropane-1,4'-1',2',3',4'-tetrahydroquinoline)-6-carboxylic acid dimethylamide;
2-(5-Chloro-2-fluoro-phenyl)-spiro(cyclopropane-1,4'-1',2',3',4'-tetrahydroquinoline)-6-carboxylic acid cyclobutylamide;
2-(5-Chloro-2-fluoro-phenyl)-spiro(cyclopropane-1,4'-1',2',3',4'-tetrahydroquinoline)-6-carboxylic acid isopropylamide;
[2-(2-Bromo-5-fluoro-phenyl)-spiro(cyclopropane-1,4'-1',2',3',4'-tetrahydroquinolin)-6-yl]-piperazin-1-yl-methanone;
2-(2-Bromo-4-fluoro-6-methyl-phenyl)-spiro(cyclopropane-1,4'-1',2',3',4'-tetrahydroquinoline)-6-carboxylic acid methylamide;
4,4-Dimethyl-2-(1-methyl-1-phenyl-ethyl)-1,2,3,4-tetrahydro-quinoline-6-carboxylic acid dimethylamide;
2-(2-Bromo-5-fluoro-phenyl)-spiro(cyclopentane-1,4'-1',2',3',4'-tetrahydroquinoline)-6-carboxylic acid dimethylamide;
2-(2-Bromo-5-fluoro-phenyl)-spiro(cyclopentane-1,4'-1',2',3',4'-tetrahydroquinoline)-6-carboxylic acid cyclopropylamide;
2-(2-Bromo-5-fluoro-phenyl)-spiro(cyclopentane-1,4'-1',2',3',4'-tetrahydroquinoline)-6-carboxylic acid (1-methyl-piperidin-4-yl)-amide;
2-(2-Bromo-5-fluoro-phenyl)-spiro(cyclopentane-1,4'-1',2',3',4'-tetrahydroquinoline)-6-carboxylic acid cyclobutylamide;
2-(2-Bromo-5-fluoro-phenyl)-spiro(cyclopentane-1,4'-1',2',3',4'-tetrahydroquinoline)-6-carboxylic acid methylamide;
2-(2-Bromo-5-fluoro-phenyl)-spiro(cyclopentane-1,4'-1',2',3',4'-tetrahydroquinoline)-6-carboxylic acid (2-hydroxy-ethyl)-amide;
[2-(2-Bromo-5-fluoro-phenyl)-spiro(cyclopentane-1,4'-1',2',3',4'-tetrahydroquinolin)-6-yl]-morpholin-4-yl-methanone;
[2-(2-Bromo-5-fluoro-phenyl)-spiro(cyclopentane-1,4'-1',2',3',4'-tetrahydroquinolin)-6-yl]-(4-methyl-piperazin-1-yl)-methanone;
2-(2-Bromo-5-fluoro-phenyl)-spiro(cyclopentane-1,4'-1',2',3',4'-tetrahydroquinoline)-6-carboxylic acid oxetan-3-ylamide;
2-(2-Bromo-5-fluoro-phenyl)-spiro(cyclopentane-1,4'-1',2',3',4'-tetrahydroquinoline)-6-carboxylic acid isopropylamide;
2-(2,5-Dichloro-phenyl)-spiro(cyclopentane-1,4'-1',2',3',4'-tetrahydroquinoline)-6-carboxylic acid cyclobutylamide;
2-(3-Fluoro-phenyl)-spiro(cyclopentane-1,4'-1',2',3',4'-tetrahydroquinoline)-6-carboxylic acid cyclobutylamide;
2-(3-Morpholin-4-yl-phenyl)-spiro(cyclopentane-1,4'-1',2',3',4'-tetrahydroquinoline)-6-carboxylic acid methylamide;
2-(5-Chloro-2-fluoro-phenyl)-spiro(cyclopentane-1,4'-1',2',3',4'-tetrahydroquinoline)-6-carboxylic acid cyclobutylamide;
2-(5-Chloro-2-fluoro-phenyl)-spiro(cyclopentane-1,4'-1',2',3',4'-tetrahydroquinoline)-6-carboxylic acid dimethylamide;
2-(2,5-Dichloro-phenyl)-4,4-dimethyl-1,2,3,4-tetrahydro-quinoline-6-carboxylic acid cyclobutylamide;
2-(5-Chloro-2-fluoro-phenyl)-4,4-dimethyl-1,2,3,4-tetrahydro-quinoline-6-carboxylic acid cyclobutylamide;
4,4-Dimethyl-2-(3-morpholin-4-yl-phenyl)-1,2,3,4-tetrahydro-quinoline-6-carboxylic acid (2-hydroxy-1-hydroxymethyl-1-methyl-ethyl)-amide;

2-(3-Chloro-4-fluoro-phenyl)-spiro(cyclopentane-1,4'-1',2', 3',4'-tetrahydroquinoline)-6-carboxylic acid cyclobutylamide;

6-(3-Chloro-4-fluoro-phenyl)-8-ethyl-8-methyl-5,6,7,8-tetrahydro-[1,5]naphthyridine-2-carboxylic acid cyclobutylamide;

4,4-Dimethyl-2-(3-morpholin-4-yl-phenyl)-1,2,3,4-tetrahydro-quinoline-6-carboxylic acid isopropylamide;

N-[2-(1,1-dioxidothiomorpholin-4-yl)ethyl]-4,4-dimethyl-2-[3-(morpholin-4-yl)phenyl]-1,2,3,4-tetrahydroquinoline-6-carboxamide;

4,4-Dimethyl-2-(3-morpholin-4-yl-phenyl)-1,2,3,4-tetrahydro-quinoline-6-carboxylic acid (2,3-dihydroxy-propyl)-amide;

N-[2-(1,1-dioxidothiomorpholin-4-yl)ethyl]-4,4-dimethyl-2-{3-[4-(propan-2-yl)piperazin-1-yl]phenyl}-1,2,3,4-tetrahydroquinoline-6-carboxamide;

N-[2-(1,1-dioxidothiomorpholin-4-yl)ethyl]-4,4-dimethyl-2-(2-phenylpropan-2-yl)-1,2,3,4-tetrahydroquinoline-6-carboxamide;

[4,4-Dimethyl-2-(1-methyl-1-phenyl-ethyl)-1,2,3,4-tetrahydro-quinolin-6-yl]-morpholin-4-yl-methanone;

[4,4-Dimethyl-2-(3-morpholin-4-yl-phenyl)-1,2,3,4-tetrahydro-quinolin-6-yl]-(3-hydroxy-3-methyl-pyrrolidin-1-yl)-methanone;

4,4-Dimethyl-2-(3-morpholin-4-yl-phenyl)-1,2,3,4-tetrahydro-quinoline-6-carboxylic acid (2-hydroxy-1-hydroxymethyl-ethyl)-amide;

4,4-Dimethyl-2-(3-morpholin-4-yl-phenyl)-1,2,3,4-tetrahydro-quinoline-6-carboxylic acid (2-hydroxy-ethyl)-amide;

[2-(3-Fluoro-5-morpholin-4-yl-phenyl)-4,4-dimethyl-1,2,3, 4-tetrahydro-quinolin-6-yl]-(3-hydroxy-3-methyl-pyrrolidin-1-yl)-methanone;

[2-(3-Fluoro-5-morpholin-4-yl-phenyl)-4,4-dimethyl-1,2,3, 4-tetrahydro-quinolin-6-yl]-morpholin-4-yl-methanone;

[4,4-Dimethyl-2-(3-morpholin-4-yl-phenyl)-1,2,3,4-tetrahydro-quinolin-6-yl]-morpholin-4-yl-methanone;

2-(3-Fluoro-5-morpholin-4-yl-phenyl)-4,4-dimethyl-1,2,3, 4-tetrahydro-quinolin-6-yl]-[3-(1-hydroxy-1-methyl-ethyl)-pyrrolidin-1-yl]-methanone;

2-(5-Fluoro-2-isopropoxy-phenyl)-4,4-dimethyl-1,2,3,4-tetrahydro-quinoline-6-carboxylic acid cyclobutylamide;

2-(5-Fluoro-2-isopropoxy-phenyl)-4,4-dimethyl-1,2,3,4-tetrahydro-quinoline-6-carboxylic acid (2-hydroxy-1-hydroxymethyl-ethyl)-amide;

[2-(5-Fluoro-2-isopropoxy-phenyl)-4,4-dimethyl-1,2,3,4-tetrahydro-quinolin-6-yl]-(3-hydroxy-3-methyl-pyrrolidin-1-yl)-methanone;

2-(3-Chloro-4-fluoro-phenyl)-4,4-dimethyl-1,2,3,4-tetrahydro-quinoline-6-carboxylic acid (1-benzyl-piperidin-4-yl)-amide;

2-(3-Fluoro-5-morpholin-4-yl-phenyl)-4,4-dimethyl-1,2,3, 4-tetrahydro-quinoline-6-carboxylic acid (2-hydroxy-ethyl)-amide; and

[4,4-Dimethyl-2-(3-morpholin-4-yl-phenyl)-1,2,3,4-tetrahydro-quinolin-6-yl]-[3-(1-hydroxy-1-methyl-ethyl)-pyrrolidin-1-yl]-methanone.

Further particular compounds of the present invention can be selected from the group consisting of:

2-(5-Fluoro-2-methyl-phenyl)-spiro(cyclopropane-1,4'-1',2', 3',4'-tetrahydroquinoline)-6-carboxylic acid;

2-(5-Bromo-2-fluoro-phenyl)-spiro(cyclopropane-1,4'-1',2', 3',4'-tetrahydroquinoline)-6-carboxylic acid;

2-(5-Chloro-2-fluoro-phenyl)-spiro(cyclopropane-1,4'-1',2', 3',4'-tetrahydroquinoline)-6-carboxylic acid;

2-(2-Bromo-5-fluoro-phenyl)-spiro(cyclopropane-1,4'-1',2', 3',4'-tetrahydroquinoline)-6-carboxylic acid;

2-(3-Fluoro-phenyl)-spiro(cyclopropane-1,4'-1',2',3',4'-tetrahydroquinoline)-6-carboxylic acid;

2-(2-Bromo-5-fluoro-phenyl)-spiro(cyclohexane-1,4'-1',2', 3',4'-tetrahydroquinoline)-6-carboxylic acid;

2-(2-Bromo-5-fluoro-phenyl)-spiro(cyclopentane-1,4'-1',2', 3',4'-tetrahydroquinoline)-6-carboxylic acid;

2-(5-Fluoro-2-methanesulfonyl-phenyl)-spiro(cyclopropane-1,4'-1',2',3',4'-tetrahydroquinoline)-6-carboxylic acid;

2-(2,5-Dichloro-phenyl)-1-dimethylcarbamoyl-spiro(cyclopropane-1,4'-1',2',3',4'-tetrahydroquinoline)-6-carboxylic acid;

1-Benzyl-2-(2,5-dichloro-phenyl)-spiro(cyclopropane-1,4'-1',2',3',4'-tetrahydroquinoline)-6-carboxylic acid;

7-Chloro-2-(5-chloro-2-fluoro-phenyl)-4,4-dimethyl-1,2,3, 4-tetrahydro-quinoline-6-carboxylic acid;

[2-(5-Chloro-2-fluoro-phenyl)-4,4-dimethyl-1,2,3,4-tetrahydro-quinolin-6-yl]-acetic acid;

2-(3-Chloro-4-fluoro-phenyl)-4-methyl-4-vinyl-1,2,3,4-tetrahydro-quinoline-6-carboxylic acid;

2-(3-Chloro-4-fluoro-phenyl)-4-methyl-4-phenyl-1,2,3,4-tetrahydro-quinoline-6-carboxylic acid;

6-(3-Chloro-4-fluoro-phenyl)-8-methyl-8-vinyl-5,6,7,8-tetrahydro-[1,5]naphthyridine-2-carboxylic acid;

6-(3-Chloro-4-fluoro-phenyl)-8-ethyl-8-methyl-5,6,7,8-tetrahydro-[1,5]naphthyridine-2-carboxylic acid;

6-(3-Chloro-4-fluoro-phenyl)-8-ethyl-8-methyl-5-(3-methyl-butyl)-5,6,7,8-tetrahydro-[1,5]naphthyridine-2-carboxylic acid;

[2-(5-Fluoro-2-methyl-phenyl)-spiro(cyclopropane-1,4'-1', 2',3',4'-tetrahydroquinolin)-6-yl]-morpholin-4-yl-methanone;

[2-(5-Fluoro-2-methyl-phenyl)-spiro(cyclopropane-1,4'-1', 2',3',4'-tetrahydroquinolin)-6-yl]-(4-methyl-piperazin-1-yl)-methanone;

[2-(2-Bromo-5-fluoro-phenyl)-spiro(cyclopropane-1,4'-1', 2',3',4'-tetrahydroquinolin)-6-yl]-morpholin-4-yl-methanone;

2-(2-Bromo-5-fluoro-phenyl)-spiro(cyclopropane-1,4'-1',2', 3',4'-tetrahydroquinoline)-6-carboxylic acid dimethylamide;

2-(2,5-Dichloro-phenyl)-spiro(cyclopropane-1,4'-1',2',3',4'-tetrahydroquinoline)-6-carboxylic acid methylamide;

2-(2,5-Dichloro-phenyl)-spiro(cyclopropane-1,4'-1',2',3',4'-tetrahydroquinoline)-6-carboxylic acid cyclobutylamide;

[2-(2,5-Dichloro-phenyl)-spiro(cyclopropane-1,4'-1',2',3',4'-tetrahydroquinolin)-6-yl]-morpholin-4-yl-methanone;

[2-(2,5-Dichloro-phenyl)-spiro(cyclopropane-1,4'-1',2',3',4'-tetrahydroquinolin)-6-yl]-(4-methanesulfonyl-piperazin-1-yl)-methanone;

[2-(5-Chloro-2-fluoro-phenyl)-spiro(cyclopropane-1,4'-1', 2',3',4'-tetrahydroquinolin)-6-yl]-morpholin-4-yl-methanone;

2-(5-Chloro-2-fluoro-phenyl)-spiro(cyclopropane-1,4'-1',2', 3',4'-tetrahydroquinoline)-6-carboxylic acid dimethylamide;

[2-(2-Bromo-5-fluoro-phenyl)-spiro(cyclopropane-1,4'-1', 2',3',4'-tetrahydroquinolin)-6-yl]-piperazin-1-yl-methanone;

2-(2-Bromo-4-fluoro-6-methyl-phenyl)-spiro(cyclopropane-1,4'-1',2',3',4'-tetrahydroquinoline)-6-carboxylic acid methylamide;

4,4-Dimethyl-2-(1-methyl-1-phenyl-ethyl)-1,2,3,4-tetrahydro-quinoline-6-carboxylic acid dimethylamide;

2-(2-Bromo-5-fluoro-phenyl)-spiro(cyclopentane-1,4'-1',2', 3',4'-tetrahydroquinoline)-6-carboxylic acid dimethylamide;

2-(2-Bromo-5-fluoro-phenyl)-spiro(cyclopentane-1,4'-1',2',3',4'-tetrahydroquinoline)-6-carboxylic acid cyclopropylamide;

2-(2-Bromo-5-fluoro-phenyl)-spiro(cyclopentane-1,4'-1',2',3',4'-tetrahydroquinoline)-6-carboxylic acid (1-methyl-piperidin-4-yl)-amide;

2-(2-Bromo-5-fluoro-phenyl)-spiro(cyclopentane-1,4'-1',2',3',4'-tetrahydroquinoline)-6-carboxylic acid cyclobutylamide;

2-(2-Bromo-5-fluoro-phenyl)-spiro(cyclopentane-1,4'-1',2',3',4'-tetrahydroquinoline)-6-carboxylic acid methylamide;

2-(2-Bromo-5-fluoro-phenyl)-spiro(cyclopentane-1,4'-1',2',3',4'-tetrahydroquinoline)-6-carboxylic acid (2-hydroxyethyl)-amide;

[2-(2-Bromo-5-fluoro-phenyl)-spiro(cyclopentane-1,4'-1',2',3',4'-tetrahydroquinolin)-6-yl]-morpholin-4-yl-methanone;

[2-(2-Bromo-5-fluoro-phenyl)-spiro(cyclopentane-1,4'-1',2',3',4'-tetrahydroquinolin)-6-yl]-(4-methyl-piperazin-1-yl)-methanone;

2-(2-Bromo-5-fluoro-phenyl)-spiro(cyclopentane-1,4'-1',2',3',4'-tetrahydroquinoline)-6-carboxylic acid isopropylamide;

2-(3-Fluoro-phenyl)-spiro(cyclopentane-1,4'-1',2',3',4'-tetrahydroquinoline)-6-carboxylic acid cyclobutylamide;

2-(3-Morpholin-4-yl-phenyl)-spiro(cyclopentane-1,4'-1',2',3',4'-tetrahydroquinoline)-6-carboxylic acid methylamide;

4,4-Dimethyl-2-(3-morpholin-4-yl-phenyl)-1,2,3,4-tetrahydro-quinoline-6-carboxylic acid (2-hydroxy-1-hydroxymethyl-1-methyl-ethyl)-amide; and 2-(3-Chloro-4-fluoro-phenyl)-spiro(cyclopentane-1,4'-1',2',3',4'-tetrahydroquinoline)-6-carboxylic acid cyclobutylamide.

The compounds of the present invention can be prepared by any conventional means. Suitable processes for synthesizing these compounds are provided in the schemes below and in the examples. In the following schemes, $R^1$, $R^2$, $R^3$, $R^4$, $R^5$, $R^6$, $R^7$, $R^8$, $R^9$, $R^{10}$, $A^1$, $A^2$, and $A^3$ are as defined above unless otherwise indicated. X is halogen.

The following abbreviations are used in the present specification.

| Abbreviations: | |
|---|---|
| d: | day or days |
| DMSO: | dimethylsulfoxide |
| g: | gram |
| h or hr: | hour |
| hrs: | hours |
| HATU: | o-(7-azabenzotriazol-1-yl)-N,N,N',N'-tetramethyluronium hexafluorophosphate |
| HPLC: | high performance liquid chromatography |
| Hz: | hertz |
| mg: | milligram |
| min: | minute or minutes |
| mL: | milliliter |
| mmol: | millimole |
| mM: | millimole per liter |
| MS(ESI): | mass spectroscopy (electron spray ionization) |
| MW: | molecular weight |
| r.t. or R.T.: | room temperature |
| quant. | quantitative |
| μg: | microgram |
| μL: | microliter |
| μM: | micro mole per liter |

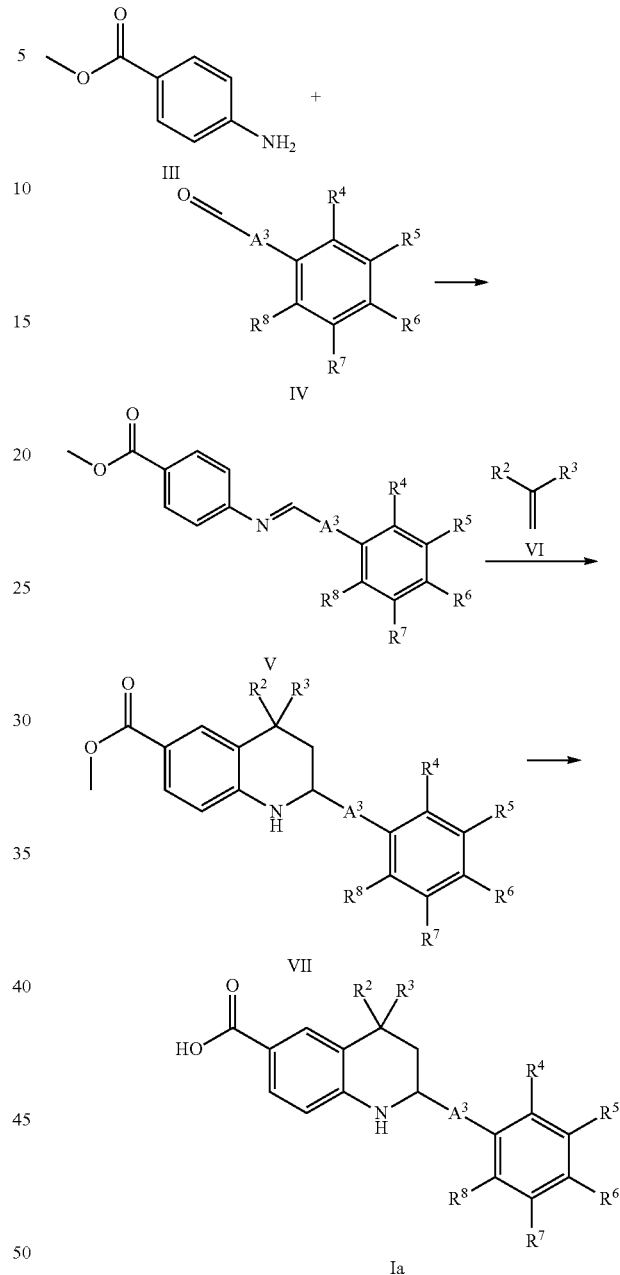

Scheme 1

$R^2$ and $R^3$ together with the carbon atom to which they are attached form cycloalkyl.

The compound of formula Ia can be prepared according to Scheme 1. The aniline III reacts with the aldehyde IV to generate the imine V. The imine V reacts with the methylene-cycloalkene VI to afford the tetrahydroquinoline VII. Hydrolysis of the tetrahydroquinoline VII affords Ia.

In the method outlined in Scheme 1, the imine V can be prepared by a condensation reaction of the substituted aniline III and the substituted aldehyde IV in an organic solvent such as toluene, methanol or ethanol and a mixture thereof, at a temperature between 80 and 140° C. for 2 to 16 hours.

The compound VII can be prepared from the imine V and the methylene-cycloalkene VI. This Diels-Alder reaction can be carried out in the presence of a Lewis acid such as ytterbium(III) trifluoromethanesulfonate (Yb(OTf)$_3$), scandium (III) trifluoromethanesulfonate (Sc(OTf)$_3$), lanthanum(III) trifluoromethanesulfonate (La(OTf)$_3$), indium(III) trifluoromethanesulfonate (In(OTf)$_3$), indium trichloride (InCl$_3$), or boron trifluoride diethyl etherate (BF$_3$.Et$_2$O), or a protic acid such as trifluoroacetic acid (TFA) or p-toluenesulfonic acid, in a solvent such as acetonitrile, dichloromethane, tetrahydrofuran, nitromethane, N,N-dimethylformamide, 2,2,2-trifluoroethanol or a mixture thereof, at a temperature between 25 and 100° C. for several hours (reference: Kiselyov, A. S. et al., *Tetrahedron* 54 (1998) 5089).

Hydrolysis of the methyl ester VII to the resulting product Ia can be carried out in the presence of an aqueous inorganic base such as lithium hydroxide, sodium hydroxide, or potassium hydroxide in a solvent such as methanol, 1,4-dioxane or tetrahydrofuran at room temperature or refluxed for several hours.

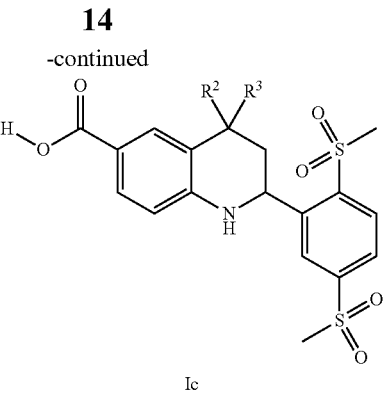

$R^2$ and $R^3$ together with the carbon atom to which they are attached form cycloalkyl.

The compound of formula Ib and Ic can be prepared according to Scheme 2. In this process, the compound of formula VIII can be synthesized as illustrated in Scheme 1. VIII is functionalized by copper-catalyzed Ullmann coupling reaction, followed by hydrolysis of the methyl ester to produce the compounds Ib and Ic.

The Ullmann coupling reaction as outlined in the Scheme 2 can be carried out in the presence of a copper source such as copper(I) iodide (CuI) or copper(II) trifluoromethanesulfonate and a ligand such as 2,2'-bipyridine, proline, N,N'-dimethyl glycine or ethylene glycol, in the presence of a suitable base such as triethylamine, sodium carbonate, potassium carbonate, cesium carbonate, sodium methoxide, sodium tert-butoxide or potassium tert-butoxide. The reaction can be carried out in a suitable solvent such as 1,4-dioxane, N,N-dimethylformamide, dimethyl sulfoxide or N-methylpyrrolidinone at a temperature between 100 and 180° C. for 15 to 60 minutes under microwave irradiation. Alternatively, the reactions can be carried out without the use of a microwave at a heated temperature such as 130° C. for a longer reaction time (reference: Ley, S. V. et al., *Angew. Chem. Int. Ed.* 42 (2003) 5400).

Hydrolysis of the methyl esters X and XI to the resulting products Ib and Ic can be carried out in the presence of an aqueous inorganic base such as lithium hydroxide, sodium hydroxide or potassium hydroxide in a solvent such as methanol, 1,4-dioxane or tetrahydrofuran at room temperature or refluxed for several hours.

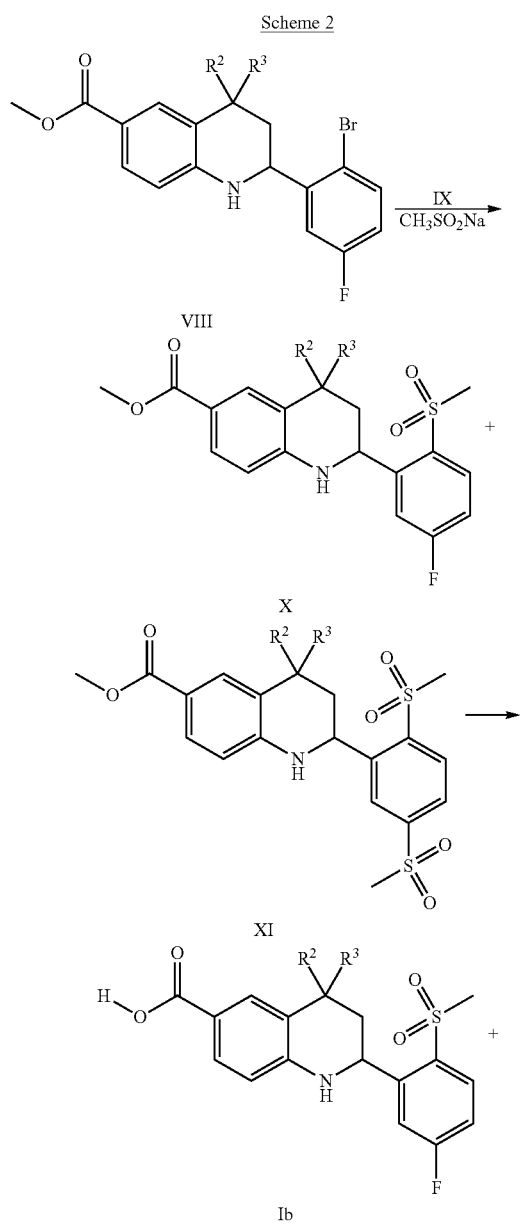

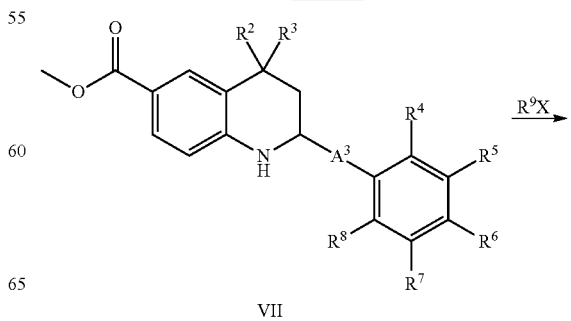

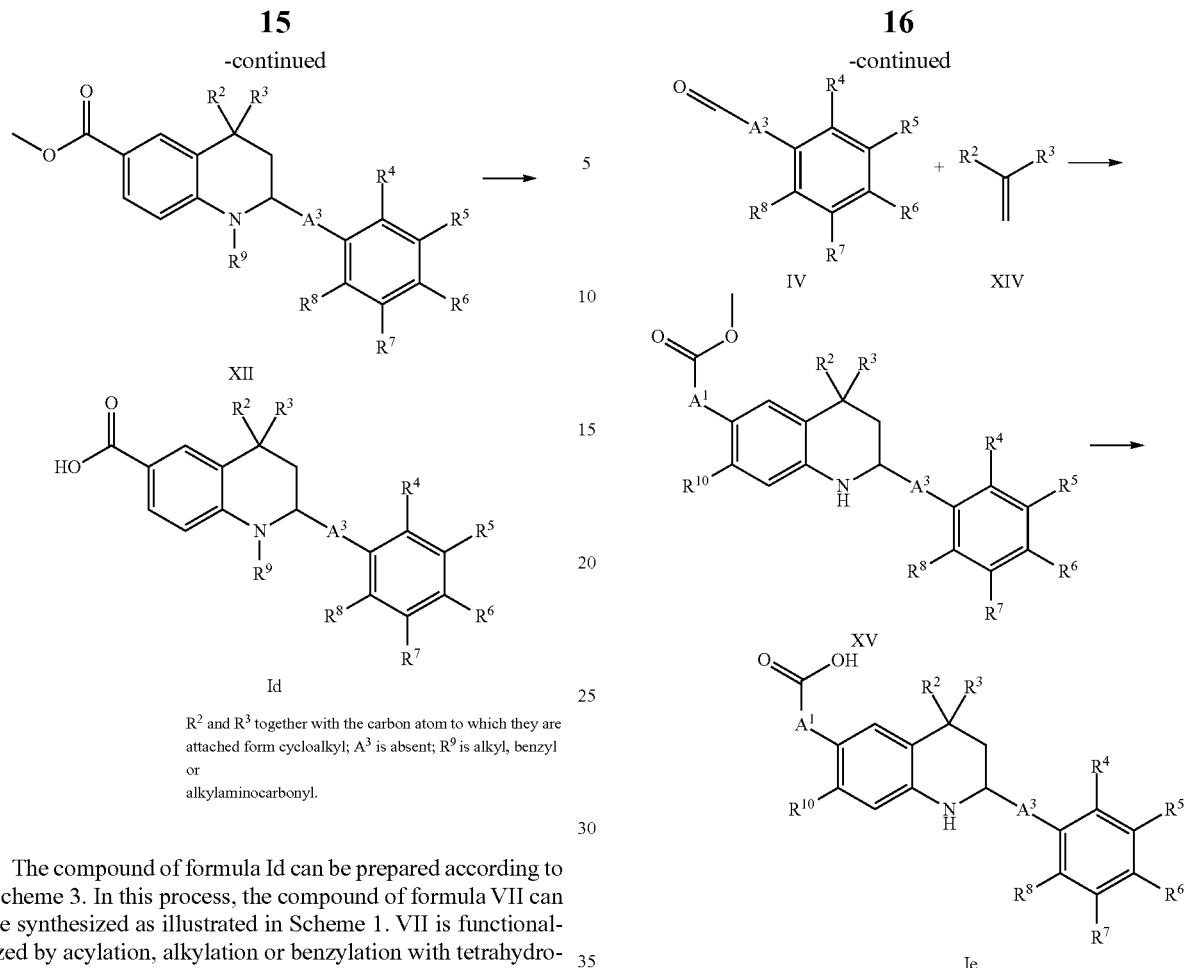

R² and R³ together with the carbon atom to which they are attached form cycloalkyl; A³ is absent; R⁹ is alkyl, benzyl or alkylaminocarbonyl.

The compound of formula Id can be prepared according to Scheme 3. In this process, the compound of formula VII can be synthesized as illustrated in Scheme 1. VII is functionalized by acylation, alkylation or benzylation with tetrahydroquinoline-1-yl group, followed by hydrolysis of the methyl ester to produce the compound Id.

Acylation, alkylation or benzylation of tetrahydro-quinoline-1-yl group of formula XII can be easily accomplished using methods well known to someone skilled in the art. The reaction is typically carried out in the presence of a base such as triethylamine, pyridine, sodium methoxide, sodium tert-butoxide, potassium tert-butoxide, sodium hydride or dimethyl-pyridin-4-yl-amine in a suitable inert solvent such as dichloromethane, acetonitrile, 1,4-dioxane, tetrahydrofuran or a mixtures thereof, at room temperature for several hours.

Hydrolysis of the methyl esters can be carried out in the presence of an aqueous inorganic base such as lithium hydroxide, sodium hydroxide or potassium hydroxide in a solvent such as methanol, 1,4-dioxane, tetrahydrofuran or a mixtures thereof at room temperature or refluxed for several hours.

Scheme 4

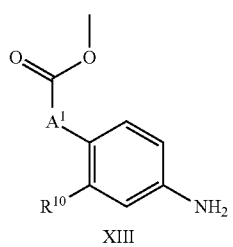

R² and R³ are independently selected from alkyl, alkenyl and phenyl.

The compound of formula Ie can be prepared according to Scheme 4. This approach is based on three-component aza-Diels-Alder reactions using a Lewis acid or protic acid as the catalyst. The substituted aniline XIII, substituted aldehyde IV and substituted ethylene XIV are used in this reaction to afford XV. The corresponding acid Ie can be afforded through hydrolysis of the methyl ester XV.

In the method outlined in Scheme 4, the compound XV can be prepared by a three-component condensation of substituted aniline XIII, substituted aldehyde IV, and substituted ethylene XIV. This reaction can be carried out successfully in the presence of a Lewis acid such as ytterbium(III) trifluoromethanesulfonate (Yb(OTf)₃), scandium(III) trifluoromethanesulfonate (Sc(OTf)₃), lanthanum(III) trifluoromethanesulfonate (La(OTf)₃), indium(III) trifluoromethanesulfonate (In(OTf)₃), indium trichloride (InCl₃) or boron trifluoride diethyl etherate (BF₃.Et₂O) or a protic acid such as trifluoroacetic acid (TFA) or p-toluenesulfonic acid, in aqueous or anhydrous conditions such as acetonitrile, dichloromethane, tetrahydrofuran, nitromethane, N,N-dimethylformamide, 2,2,2-trifluoroethanol, water or a mixture thereof, at a temperature between 25 and 100° C. for several hours (reference: Kiselyov, A. S. et al., *Tetrahedron* 54 (1998) 5089).

Hydrolysis of the methyl ester XV to the resulting product Ie can be carried out in the presence of an aqueous inorganic base such as lithium hydroxide, sodium hydroxide or potassium hydroxide in a solvent such as methanol, 1,4-dioxane, tetrahydrofuran or a mixture thereof at room temperature or refluxed for several hours.

Scheme 5

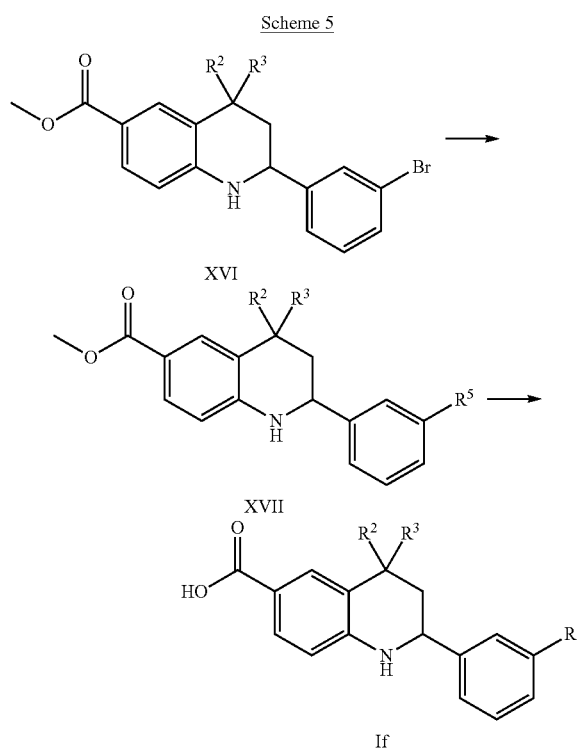

$R^2$ and $R^3$ are alkyl;
$R^5$ is morpholinyl, piperazinyl or alkylpiperazinyl.

The compound of formula If can be prepared according to Scheme 5. In this process, the compound of formula XVI can be synthesized as illustrated in Scheme 4. XVI is functionalized by copper-catalyzed Ullmann coupling reaction with amine such as morpholine, piperazine or N-methyl-piperazine or sodium methanesulfinate, followed by hydrolysis of the methyl ester to produce the compound If.

The Ullmann coupling reaction as outlined in the Scheme 5 can be carried out in the presence of a copper source such as copper(I) iodide (CuI) or copper(II) trifluoromethanesulfonate and a ligand such as 2,2'-bipyridine, proline, N,N'-dimethyl glycine or ethylene glycol, in the presence of a suitable base such as triethylamine, potassium carbonate or cesium carbonate. The reaction can be carried out in a suitable solvent such as 1,4-dioxane, N,N-dimethylformamide, dimethyl sulfoxide or N-methylpyrrolidinone at a temperature between 100 and 180° C. for 15 to 60 minutes under microwave irradiation. Alternatively, the reactions can be carried out without the use of a microwave at high temperature such as 130° C. for a longer reaction time (reference: Ley, S. V. et al., *Angew. Chem. Int. Ed.* 42 (2003) 5400).

Hydrolysis of the methyl ester XVII to the resulting product If can be carried out in the presence of an aqueous inorganic base such as lithium hydroxide, sodium hydroxide or potassium hydroxide in a solvent such as methanol, 1,4-dioxane, tetrahydrofuran or a mixture thereof at room temperature or refluxed for several hours.

Scheme 6

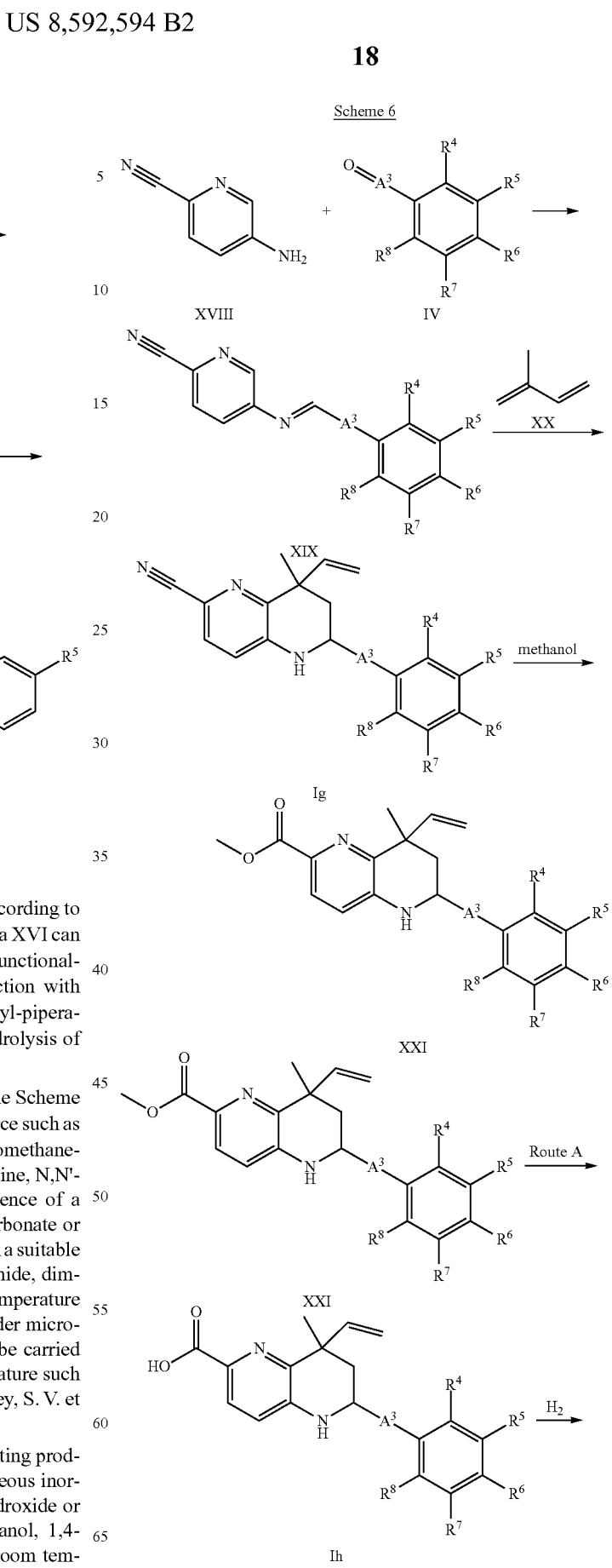

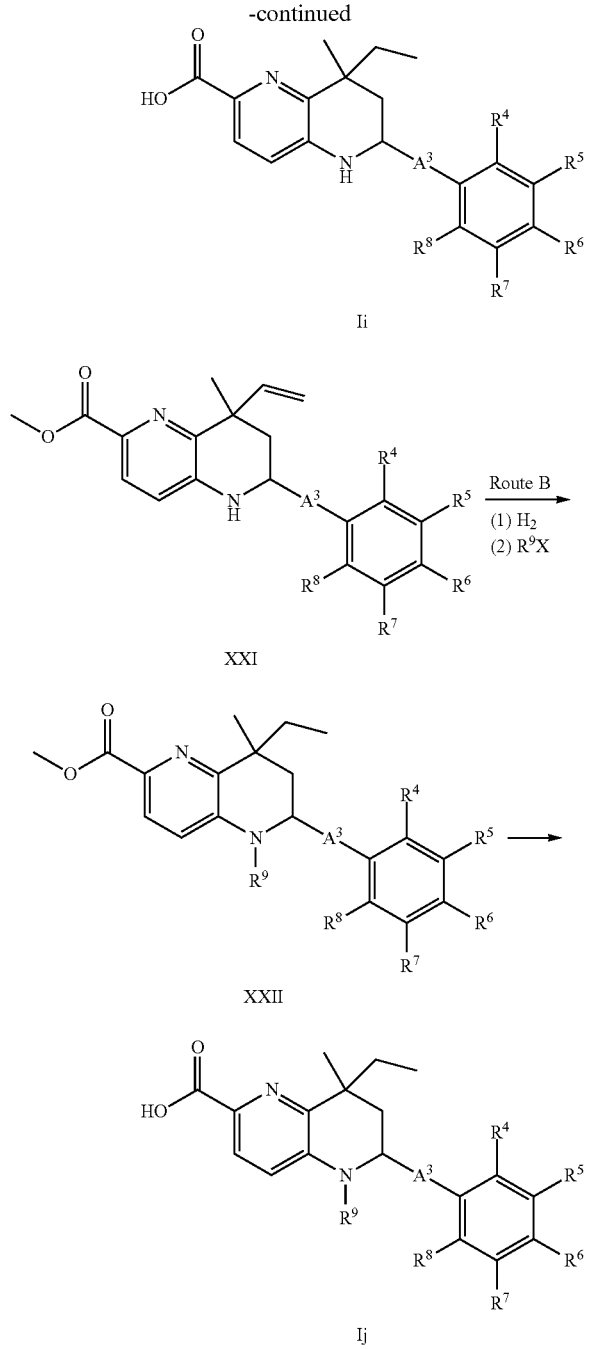

$A^3$ is absent; $R^4$, $R^5$, $R^6$, $R^7$, $R^8$ are independently selected from hydrogen and halogen; $R^9$ is alkyl.

$A^3$ is absent; $R^4$, $R^5$, $R^6$, $R^7$, $R^8$ are independently selected from hydrogen and halogen; $R^9$ is alkyl.

The compounds of formula Ig, Ih, Ii and Ij can be prepared according to Scheme 6. This approach is based on two-component Diels-Alder reactions using a Lewis acid or protic acid as the catalyst. Condensation of the compound of XVIII and substituted aldehyde IV generates imine XIX. Imine XIX and 2-methyl-buta-1,3-diene XX are used in this reaction to afford Ig. The corresponding methyl ester XXI can be formed by methanolysis of nitrile Ig, followed by hydrolysis of the methyl ester (Route A) to produce the compound Ih. Reduction of the vinyl compound Ih to the corresponding derivative Ii can be accomplished using methods well known to someone skilled in the art. The corresponding acid Ij can be prepared through hydrogenation of compound XXI (Route B), followed by acylation and hydrolysis of the methyl ester XXII.

In the method outlined in Scheme 6, the imine XIX can be prepared from 5-amino-pyridine-2-carbonitrile XVIII and substituted aldehyde IV. The compound Ig can be prepared from imine XIX and 2-methyl-buta-1,3-diene XX through Diels-Alder reactions. This Diels-Alder reaction can be carried out successfully in the presence of a Lewis acid such as ytterbium(III) trifluoromethanesulfonate ($Yb(OTf)_3$), scandium(III) trifluoromethanesulfonate ($Sc(OTf)_3$), lanthanum (III) trifluoromethanesulfonate ($La(OTf)_3$), indium(III) trifluoromethanesulfonate ($In(OTf)_3$), indium trichloride ($InCl_3$) or boron trifluoride diethyl etherate ($BF_3.Et_2O$) or a protic acid such as trifluoroacetic acid (TFA) or p-toluenesulfonic acid, in a solvent such as acetonitrile, dichloromethane, tetrahydrofuran, nitromethane, N,N-dimethylformamide, 2,2,2-trifluoroethanol, water or a mixture thereof, at a temperature between 25 and 100° C. for several hours (reference: Kiselyov, A. S. et al., *Tetrahedron* 54 (1998) 5089).

Methanolysis of the nitrile Ig can provide the corresponding methyl ester XXI. The reaction can be carried out in the presence of a catalyst such as hydrochloride, concentrated sulfuric acid, chlorotrimethylsilane or thionyl chloride in methanol, at a temperature between room temperature and 90° C. for several hours.

Hydrolysis of the methyl ester XXI (Route A) to the resulting product Ih can be carried out in the presence of an aqueous inorganic base such as lithium hydroxide, sodium hydroxide or potassium hydroxide in a solvent such as methanol, 1,4-dioxane, tetrahydrofuran or a mixture thereof at room temperature or refluxed for several hours.

Hydrogenation of the vinyl compound Ih to the corresponding Ii can be accomplished using methods well known to someone skilled in the art. The reaction is typically carried out under 10% palladium on active carbon in a suitable solvent such as methanol, ethanol, tetrahydrofuran, water or a mixture thereof at room temperature or reflux of the solvent for several hours.

Hydrogenation of the vinyl compound XXI (Route B) can be accomplished using methods well known to someone skilled in the art. The reaction typically is carried out under 10% palladium on active carbon in a suitable solvent such as methanol, ethanol, tetrahydrofuran, water or a mixture thereof at room temperature or reflux of the solvent for several hours.

Acylation, alkylation or benzylation of the tetrahydroquinoline-1-yl group of formula XXII can be easily accomplished using methods well known to someone skilled in the art. The reaction is typically carried out in the presence of a base such as triethylamine, pyridine, sodium methoxide, sodium tert-butoxide, potassium tert-butoxide, sodium hydride or dimethyl-pyridin-4-yl-amine in a suitable inert solvent such as dichloromethane, acetonitrile, 1,4-dioxane, tetrahydrofuran or mixtures thereof, at room temperature for several hours.

Hydrolysis of the methyl ester XXII to the resulting product Ij can be carried out in the presence of an aqueous inorganic base such as lithium hydroxide, sodium hydroxide or potassium hydroxide in a solvent such as methanol, 1,4-dioxane, tetrahydrofuran or a mixture thereof at room temperature or refluxed for several hours.

Scheme 7

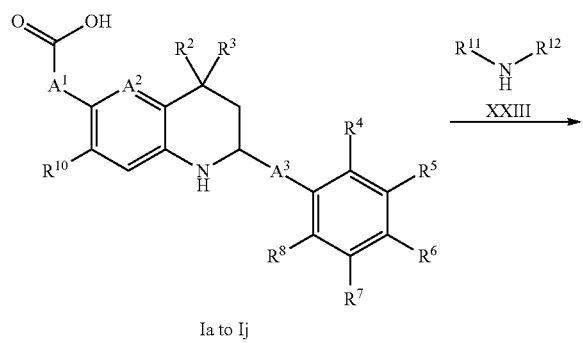

Ia to Ij

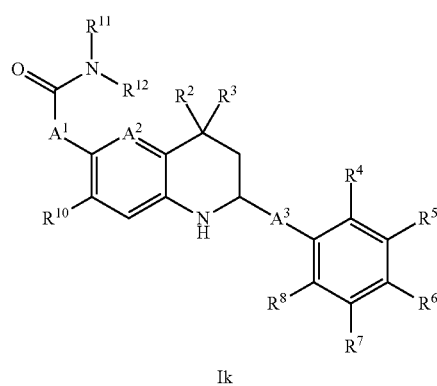

Ik

The compound of formula Ik can be synthesized as illustrated in Scheme 7, starting from the one compound selected from Ia to Ij, which can be prepared according to Schemes 1-6.

Conversion of the acids Ia to Ij to the corresponding amide Ik with suitable amines XXIII can be easily accomplished using methods well known to someone skilled in the art. The reaction is typically carried out in the presence of a coupling reagent such as dicyclohexyl carbodiimide (DCC), benzotriazol-1-yl-oxy-tris-pyrrolidinophosphonium hexafluorophosphate (PyBop), o-(7-azabenzotriazol-1-yl)-N,N,N',N'-tetramethyluronium hexafluorophosphate (HATU), o-(1H-benzotriazol-1-yl)-N,N,N',N'-tetramethyluronium hexafluorophosphate (HBTU) or 1-ethyl-3-(3'-dimethylamino)carbodiimide hydrochloride salt (EDCI), in the presence or absence of hydroxybenzotriazole (HOBt), in the presence of a base such as triethylamine or N,N-diisopropyl ethylamine or N,N-dimethylaminopyridine (DMAP). The reaction can be carried out in a solvent such as dichloromethane or N,N-dimethylformamide at room temperature for several hours (reference: Montalbetti, C. A. G. N. et al., *Tetrahedron* 61 (2005) 10827).

The invention also relates to a process for the preparation of a compound of formula (I) comprising one of the following steps:

(a) the reaction of a compound of formula (A)

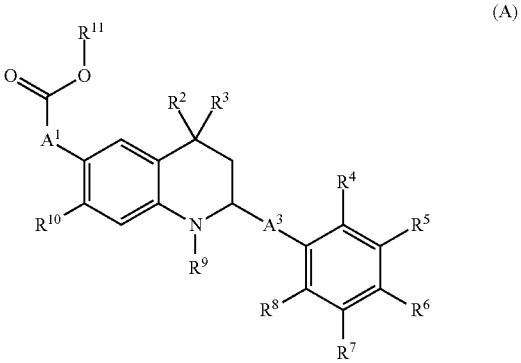

in the presence of a base; or
(b) the reaction of a compound of formula (B)

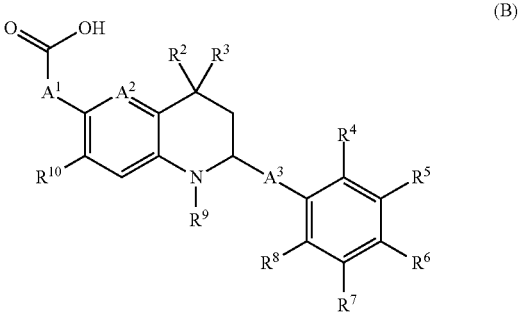

in the presence of a coupling agent and a base;
wherein $R^1, R^2, R^3, R^4, R^5, R^6, R^7, R^8, R^9, R^{10}, A^1, A^2,$ and $A^3$ are defined above and $R^{11}$ is alkyl. $R^{11}$ is preferably methyl.

In step (a), the base can be for example be independently selected form lithium hydroxide, sodium hydroxide or potassium hydroxide.

In step (b), the coupling reagent can be for example dicyclohexyl carbodiimide (DCC), benzotriazol-1-yl-oxy-tris-pyrrolidinophosphonium hexafluorophosphate (PyBop), o-(7-azabenzotriazol-1-yl)-N,N,N',N'-tetramethyluronium hexafluorophosphate (HATU), o-(1H-benzotriazol-1-yl)-N,N',N'-tetramethyluronium hexafluorophosphate (HBTU) or 1-ethyl-3-(3'-dimethylamino)carbodiimide hydrochloride salt (EDCI). Step (i) can be carried out in the presence or absence of hydroxybenzotriazole (HOBt), in the presence of a base such as triethylamine or N,N-diisopropyl ethylamine or N,N-dimethylaminopyridine (DMAP).

The invention also relates to a compound of formula (I), or a pharmaceutically acceptable salt or ester thereof, for use as therapeutically active substance.

The invention also relates to a pharmaceutical composition comprising a compound of formula (I), or a pharmaceutically acceptable salt or ester thereof, and a therapeutically inert carrier.

The use of a compound of formula (I), or a pharmaceutically acceptable salt or ester thereof, for the preparation of medicaments useful in the treatment or prophylaxis diseases that are related to AMPK regulation is an object of the invention.

The invention relates in particular to the use of a compound of formula (I), or a pharmaceutically acceptable salt or ester thereof, for the preparation of a medicament for the treatment or prophylaxis of obesity, dyslipidemia, hyperglycemia, type 1 or type 2 diabetes, in particular type 2 diabetes.

Said medicaments, e.g. in the form of pharmaceutical preparations, can be administered orally, e.g. in the form of tablets, coated tablets, dragées, hard and soft gelatine capsules, solutions, emulsions or suspensions. The administration can, however, also be effected rectally, e.g. in the form of suppositories, or parenterally, e.g. in the form of injection solutions with an effective amount of a compound as defined above.

The above-mentioned pharmaceutical composition can be obtained by processing the compounds according to this invention with pharmaceutically inert inorganic or organic carriers. Lactose, corn starch or derivatives thereof, talc, stearic acids or its salts and the like can be used, for example, as such carriers (or excipients) for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical composition can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The dosage depends on various factors such as manner of administration, species, age and/or individual state of health. The doses to be administered daily are about 5-400 mg/kg, preferably about 10-100 mg/kg, and can be taken singly or distributed over several administrations.

A compound of formula (I) when manufactured according to the above process is also an object of the invention.

Furthermore, the invention also relates to a method for the treatment or prophylaxis of diseases that are related to AMPK regulation, which method comprises administering an effective amount of a compound of formula (I), or a pharmaceutically acceptable salt or ester thereof.

The invention further relates to a method for the treatment or prophylaxis of obesity, dyslipidemia, hyperglycemia, type 1 or type 2 diabetes, in particular type 2 diabetes, which method comprises administering an effective amount of a compound of formula (I), or a pharmaceutically acceptable salt or ester thereof.

Furthermore, the invention also relates to a compound of formula (I), or a pharmaceutically acceptable salt or ester thereof, for the preparation of medicaments useful in the treatment of cancers that are related to AMPK regulation. The invention provides a method for the treatment of cancers that are related to AMPK regulation, which method comprises administering an effective amount of a compound of formula (I), or a pharmaceutically acceptable salt or ester thereof.

The invention will be illustrated by the following examples which have no limiting character. Unless explicitly otherwise stated, all reactions, reaction conditions, abbreviations and symbols have the meanings well known to a person of ordinary skill in organic chemistry.

EXAMPLES

Materials and Instrumentation

Intermediates and final compounds were purified by flash chromatography using one of the following instruments: i) Biotage SP1 system and the Quad 12/25 Cartridge module. ii) ISCO combi-flash chromatography instrument. Silica gel Brand and pore size: i) KP-SIL 60 Å, particle size: 40-60 μM; ii) CAS registry NO: Silica Gel: 63231-67-4, particle size: 47-60 micron silica gel; iii) ZCX from Qingdao Haiyang Chemical Co., Ltd, pore: 200-300 or 300-400.

Intermediates and final compounds were purified by preparative HPLC on reversed phase column using X Bridge™ Perp C18 (5 μm, OBD™ 30×100 mm) column or SunFire™ Perp C18 (5 μm, OBD™ 30×100 mm) column.

LC/MS spectra were obtained using a MicroMass Plateform LC (Waters™ alliance 2795-ZQ2000). Standard LC/MS conditions were as follows (running time 6 min):

Acidic condition: A: 0.1% formic acid in $H_2O$; B: 0.1% formic acid in acetonitrile;

Basic condition: A: 0.01% $NH_3.H_2O$ in $H_2O$; B: acetonitrile;

Neutral condition: A: $H_2O$; B: acetonitrile.

Mass spectra (MS): generally only ions which indicate the parent mass are reported, and unless otherwise stated the mass ion quoted is the positive mass ion-$(M+H)^+$.

The microwave assisted reactions were carried out in a Biotage Initiator Sixty.

NMR Spectra were obtained using Bruke Avance 400 MHz.

All reactions involving air-sensitive reagents were performed under an argon atmosphere. Reagents were used as received from commercial suppliers without further purification unless otherwise noted.

Example 1

2-(5-Fluoro-2-methyl-phenyl)-spiro(cyclopropane-1, 4'-1',2',3',4'-tetrahydroquinoline)-6-carboxylic acid

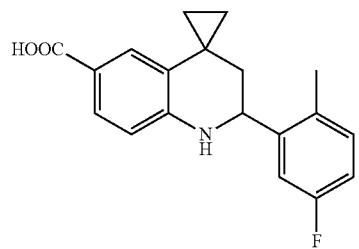 [SMILES: Cc1ccc(F)cc1C1CC2(CC2)c2cc(C(=O)O)ccc2N1]

4-[(5-Fluoro-2-methyl-benzylidene)-amino]-benzoic acid methyl

A mixture of 4-aminobenzoic acid methyl ester (10.8 g, 71.4 mmol), 5-fluoro-2-methylbenzaldehyde (10.0 g, 72.4 mmol) and p-toluenesulfonic acid (271.8 mg, 1.4 mmol) in toluene (150 mL) was heated to reflux for 12 hours. Then the reaction mixture was cooled to room temperature. The solvent was removed in vacuo and the residue was washed with ether to afford 4-[(5-fluoro-2-methyl-benzylidene)-amino]-benzoic acid methyl (16.0 g, 82.6%) as a light yellow solid. MS ($ESI^+$) $[(M+H)^+]$ 272.0.

2-(5-Fluoro-2-methyl-phenyl)-spiro(cyclopropane-1,4'-1',2',3',4'-tetrahydroquinoline)-6-carboxylic acid methyl ester To a stirred solution 4-[(5-fluoro-2-methyl-benzylidene)-amino]-benzoic acid methyl (2.7 g, 10 mmol) in MeCN (6 mL) were added methylene-cyclopropane (2.8 mL, 40 mol) and scandium(III) trifluoromethanesulfonate (Sc(OTf)$_3$) (980 mg, 2 mmol). The resulting mixture was stirred at 80° C. for 16 hours in sealed tube. The mixture was extracted with diethyl ether (80 mL) and washed with water (100 mL) and brine (100 mL) and then dried over anhydrous Na$_2$SO$_4$. The solvent was removed in vacuo and the residue was purified by ISCO combi-flash chromatography (gradient elution, 0-10% ethyl acetate in petroleum ether) to afford 2-(5-fluoro-2-methyl-phenyl)-spiro(cyclopropane-1,4'-1',2',3',4'-tetrahydroquinoline)-6-carboxylic acid methyl ester (1.2 g, 37%) as a light yellow solid. MS (ESI$^+$) [(M+H)$^+$] 326.2.

2-(5-Fluoro-2-methyl-phenyl)-spiro(cyclopropane-1,4'-1',2',3',4'-tetrahydroquinoline)-6-carboxylic acid To a solution of 2-(5-fluoro-2-methyl-phenyl)-spiro(cyclopropane-1,4'-1',2',3',4'-tetrahydroquinoline)-6-carboxylic acid methyl ester (800 mg, 2.5 mmol) in tetrahydrofuran (4 mL) and methanol (4 mL) was added 3 N sodium hydroxide (2 mL). The reaction mixture was stirred at 80° C. for 6 hours, and then diluted with water (10 mL), extracted with diethyl ether (20 mL). The organic layer was discarded. The aqueous layer was acidified with concentrated hydrochloric acid to pH 4 and extracted with ethyl acetate (40 mL×3). The combined organic layers were dried over anhydrous Na$_2$SO$_4$. The solvent was removed in vacuo and purified by preparative HPLC to afford 2-(5-fluoro-2-methyl-phenyl)-spiro(cyclopropane-1,4'-1',2',3',4'-tetrahydroquinoline)-6-carboxylic acid (650 mg, 85%) as a light yellow powder. MS (ESI$^+$) [(M+H)$^+$] 312.3.

Example 2

2-(5-Bromo-2-fluoro-phenyl)-spiro(cyclopropane-1,4'-1',2',3',4'-tetrahydroquinoline)-6-carboxylic acid

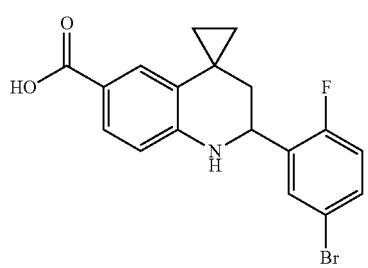

The title compound was prepared in analogy to example 1 starting from 5-Bromo-2-fluoro-benzaldehyde. MS (ESI$^+$) [(M+H)$^+$] 376.0, 378.0.

Example 3

2-(2,5-Dichloro-phenyl)-spiro(cyclopropane-1,4'-1',2',3',4'-tetrahydroquinoline)-6-carboxylic acid

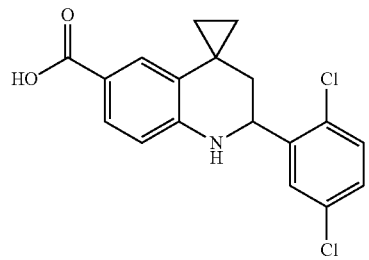

The title compound was prepared in analogy to example 1 starting from 2,5-dichloro-benzaldehyde. MS (ESI$^+$) [(M+H)$^+$] 348.1.

Example 4

2-(3,5-Dichloro-phenyl)-spiro(cyclopropane-1,4'-1',2',3',4'-tetrahydroquinoline)-6-carboxylic acid

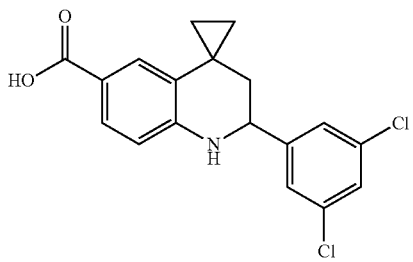 [SMILES: O=C(O)c1ccc2c(c1)C1(CC1)CC(c1cc(Cl)cc(Cl)c1)N2]

The title compound was prepared in analogy to example 1 starting from 3,5-dichloro-benzaldehyde. MS (ESI$^+$) [(M+H)$^+$] 348.1.

Example 5

2-(5-Chloro-2-fluoro-phenyl)-spiro(cyclopropane-1,4'-1',2',3',4'-tetrahydroquinoline)-6-carboxylic acid

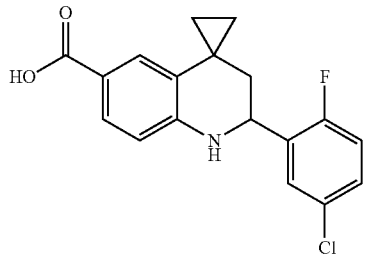 [SMILES: O=C(O)c1ccc2c(c1)C1(CC1)CC(c1cc(Cl)ccc1F)N2]

The title compound was prepared in analogy to example 1 starting from 5-chloro-2-fluoro-benzaldehyde. MS (ESI$^+$) [(M+H)$^+$] 332.2.

Example 6

2-(3-Methanesulfonyl-phenyl)-spiro(cyclopropane-1,
4'-1',2',3',4'-tetrahydroquinoline)-6-carboxylic acid

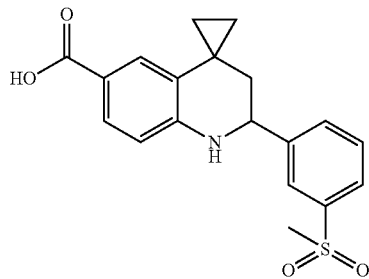 [SMILES: CS(=O)(=O)c1cccc(C2CC3(CC3)c3cc(C(=O)O)ccc3N2)c1]

The title compound was prepared in analogy to example 1 starting from 3-Methanesulfonyl-benzaldehyde. MS (ESI$^+$) [(M+H)$^+$] 358.1.

Example 7

2-(2-Bromo-5-fluoro-phenyl)-spiro(cyclopropane-1,
4'-1',2',3',4'-tetrahydroquinoline)-6-carboxylic acid

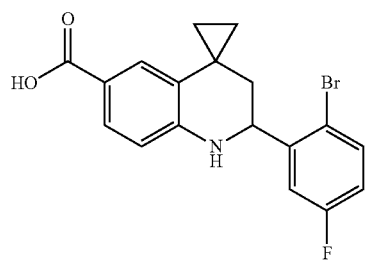 [SMILES: O=C(O)c1ccc2c(c1)C1(CC1)CC(c1cc(F)ccc1Br)N2]

The title compound was prepared in analogy to example 1 starting from 2-bromo-5-fluoro-benzaldehyde. MS (ESI$^+$) [(M+H)$^+$] 376.0, 378.0.

Example 8

2-(3-Fluoro-phenyl)-spiro(cyclopropane-1,4'-1',2',3',
4'-tetrahydroquinoline)-6-carboxylic acid

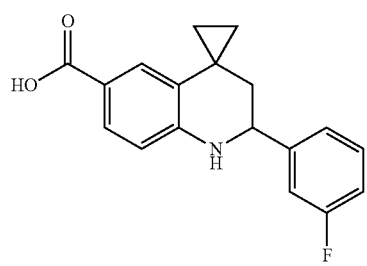 [SMILES: O=C(O)c1ccc2c(c1)C1(CC1)CC(c1cccc(F)c1)N2]

The title compound was prepared in analogy to example 1 starting from 3-fluoro-benzaldehyde. MS (ESI$^+$) [(M+H)$^+$] 298.2.

Example 9

2-(2-Bromo-5-fluoro-phenyl)-spiro(cyclohexane-1,
4'-1',2',3',4'-tetrahydroquinoline)-6-carboxylic acid

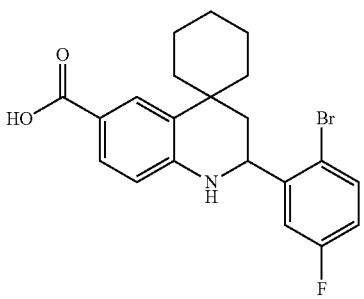 [SMILES: O=C(O)c1ccc2c(c1)C1(CCCCC1)CC(c1cc(F)ccc1Br)N2]

The title compound was prepared in analogy to example 1 starting from 2-bromo-5-fluoro-benzaldehyde. MS (ESI$^+$) [(M+H)$^+$] 418.0, 420.0.

Example 10

2-(2-Bromo-5-fluoro-phenyl)-spiro(cyclopentane-1,
4'-1',2',3',4'-tetrahydroquinoline)-6-carboxylic acid

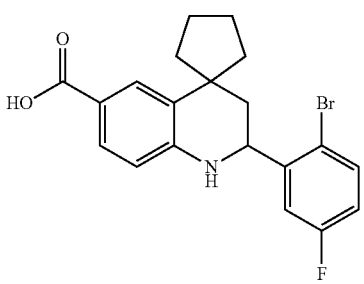 [SMILES: O=C(O)c1ccc2c(c1)C1(CCCC1)CC(c1cc(F)ccc1Br)N2]

The title compound was prepared in analogy to example 1 starting from 2-bromo-5-fluoro-benzaldehyde. MS (ESI$^+$) [(M+H)$^+$] 404.0, 406.0.

Example 11

2-(5-Fluoro-2-methanesulfonyl-phenyl)-spiro(cyclopropane-1,4'-1',2',3',4'-tetrahydroquinoline)-6-carboxylic acid

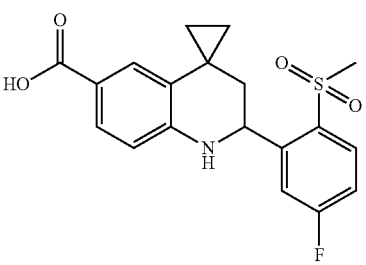 [SMILES: CS(=O)(=O)c1ccc(F)cc1C1CC2(CC2)c2cc(C(=O)O)ccc2N1]

2-(5-Fluoro-2-methanesulfonyl-phenyl)-spiro(cyclopropane-1,4'-1',2',3',4'-tetrahydroquinoline)-6-carboxylic acid methyl ester 2-(2,5-Dimethanesulfonyl-phenyl)-spiro(cyclopropane-1,4'-1',2',3',4'-tetrahydroquinoline)-6-carboxylic acid methyl ester The mixture of 2-(2-bromo-5-fluoro-phenyl)-spiro(cyclopropane-1,4'-1',2',3',4'-tetrahydroquinoline)-6-carboxylic acid methyl ester (390 mg, 1 mmol) (prepared as in example 1 starting from 2-bromo-5-fluoro-benzaldehyde), CuI (60 mg, 0.3 mmol), L-proline (70 mg, 0.6 mmol) and methanesulfinic acid, sodium salt (510 mg, 5 mmol) in DMSO (5 mL) was stirred at 120° C. for 16 hours under a nitrogen atmosphere. The reaction mixture was diluted with water (20 mL), extracted with ethyl acetate (20 mL×3) and washed with brine (100 mL) and then dried over anhydrous $Na_2SO_4$. The solvent was removed in vacuo and the residue was purified by ISCO combi-flash chromatography (gradient elution, 30-60% ethyl acetate in petroleum ether) to afford 2-(5-fluoro-2-methanesulfonyl-phenyl)-spiro(cyclopropane-1,4'-1',2',3',4'-tetrahydroquinoline)-6-carboxylic acid methyl ester (160 mg, 41.1%) as a white solid. MS (ESI$^+$) [(M+H)$^+$] 390. And side-product 2-(2,5-dimethanesulfonyl-phenyl)-spiro(cyclopropane-1,4'-1',2',3',4'-tetrahydroquinoline)-6-carboxylic acid methyl ester (120 mg, 30%) was also obtained as a white solid. MS (ESI$^+$) [(M+H)$^+$] 450.2.

2-(5-Fluoro-2-methanesulfonyl-phenyl)-spiro(cyclopropane-1,4'-1',2',3',4'-tetrahydroquinoline)-6-carboxylic acid To a solution of 2-(5-fluoro-2-methanesulfonyl-phenyl)-spiro(cyclopropane-1,4'-1',2',3',4'-tetrahydroquinoline)-6-carboxylic acid methyl ester (100 mg, 0.3 mmol) in tetrahydrofuran (2 mL) and methanol (2 mL) was added 3 N sodium hydroxide (1 mL). The reaction mixture was stirred at 80° C. for 6 hours, and then diluted with water (10 mL), extracted with diethyl ether (20 mL). The organic layer was discarded. The aqueous layer was acidified with concentrated hydrochloric acid to pH 4 and extracted with ethyl acetate (40 mL×3), and the combined organics were dried over anhydrous $Na_2SO_4$. The solvent was removed in vacuo and purified by preparative HPLC to afford 2-(5-fluoro-2-methanesulfonyl-phenyl)-spiro(cyclopropane-1,4'-1',2',3',4'-tetrahydroquinoline)-6-carboxylic acid (35 mg, 35.9%) as a yellow foam. MS (ESI$^+$) [(M+H)$^+$] 376.1.

Example 12

2-(2,5-Dimethanesulfonyl-phenyl)-spiro(cyclopropane-1,4'-1',2',3',4'-tetrahydroquinoline)-6-carboxylic acid

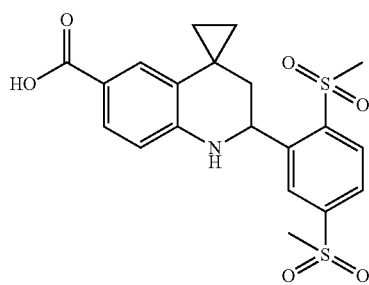 [SMILES: CS(=O)(=O)c1ccc(S(C)(=O)=O)c(C2CC3(CC3)c3cc(C(=O)O)ccc3N2)c1]

The title compound was prepared as a white powder in analogy to Example 11 starting from 2-(2,5-dimethanesulfonyl-phenyl)-spiro(cyclopropane-1,4'-1',2',3',4'-tetrahydroquinoline)-6-carboxylic acid methyl ester. MS (ESI$^+$) [(M+H)$^+$] 436.2.

Example 13

2-(2,5-Dichloro-phenyl)-1-dimethylcarbamoyl-spiro(cyclopropane-1,4'-1',2',3',4'-tetrahydroquinoline)-6-carboxylic acid

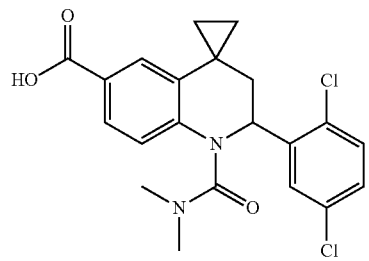 [SMILES: CN(C)C(=O)N1c2ccc(C(=O)O)cc2C2(CC2)CC1c1cc(Cl)ccc1Cl]

2-(2,5-Dichloro-phenyl)-1-dimethylcarbamoyl-spiro(cyclopropane-1,4'-1',2',3',4'-tetrahydroquinoline)-6-carboxylic acid methyl ester To a 0° C. solution of 2-(2,5-dichloro-phenyl)-spiro(cyclopropane-1,4'-1',2',3',4'-tetrahydroquinoline)-6-carboxylic acid methyl ester as prepared according to Example 1 (200 mg, 0.6 mmol) in N,N-dimethylformamide (5 mL) was added a 60% dispersion of sodium hydride in mineral oil (44 mg, 1.1 mmol) portionwise. The mixture was stirred at 0° C. for 30 min and then dimethylcarbamoyl chloride (177 mg, 1.6 mmol) was added to above mixture dropwise at 0° C. The mixture was stirred at 0° C. for 3 hours and then extracted with ethyl acetate, washed with brine, dried over anhydrous sodium sulfate and concentrated in vacuo. The yellowish residue was purified by ISCO combi-flash chromatography (gradient elution, 5% ethyl acetate/hexane) to afford 2-(2,5-dichloro-phenyl)-1-dimethylcarbamoyl-spiro(cyclopropane-1,4'-1',2',3',4'-tetrahydroquinoline)-6-carboxylic acid methyl ester (100 mg, 42.2%) as a yellow oil. MS (ESI$^+$) [(M+H)$^+$] 433.0.

2-(2,5-Dichloro-phenyl)-1-dimethylcarbamoyl-spiro(cyclopropane-1,4'-1',2',3',4'-tetrahydroquinoline)-6-carboxylic acid To a solution of 2-(2,5-dichloro-phenyl)-1-dimethylcarbamoyl-spiro(cyclopropane-1,4'-1',2',3',4'-tetrahydroquinoline)-6-carboxylic acid methyl ester (50 mg, 0.1 mmol) in tetrahydrofuran (2 mL) and methanol (2 mL) was added 3 N sodium hydroxide (0.5 mL). The reaction mixture was stirred at 80° C. for 4 hours, and then diluted with water (10 mL), extracted with diethyl ether (20 mL). The organic layer was discarded. The aqueous layer was acidified with concentrated hydrochloric acid to pH 4 and extracted with ethyl acetate (40 mL×3), and the combined organics were dried over anhydrous $Na_2SO_4$ The solvent was removed in vacuo and purified by preparative HPLC to afford 2-(2,5-dichloro-phenyl)-1-dimethylcarbamoyl-spiro(cyclopropane-1,4'-1',2',3',4'-tet-

Example 14

1-Benzyl-2-(2,5-dichloro-phenyl)-spiro(cyclopropane-1,4'-1',2',3',4'-tetrahydroquinoline)-6-carboxylic acid

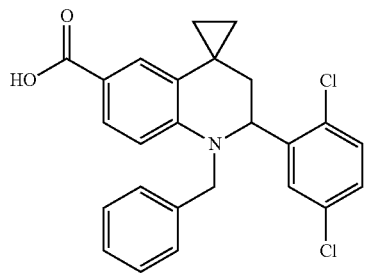 [SMILES: O=C(O)c1ccc2c(c1)C1(CC1)CC(c1cc(Cl)ccc1Cl)N2Cc1ccccc1]

The title compound was prepared as a yellow foam in analogy to Example 13 starting from 2-(2,5-dichloro-phenyl)-spiro(cyclopropane-1,4'-1',2',3',4'-tetrahydroquinoline)-6-carboxylic acid methyl ester prepared according to Example 1. MS (ESI⁺) [(M+H)⁺] 438.1.

Example 15

2-(2,5-Dichloro-phenyl)-4,4-dimethyl-1,2,3,4-tetrahydro-quinoline-6-carboxylic acid

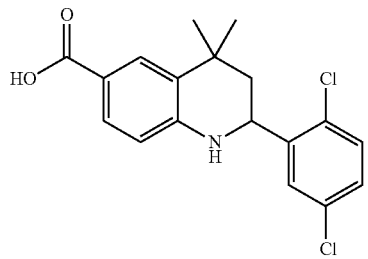 [SMILES: CC1(C)CC(c2cc(Cl)ccc2Cl)Nc2ccc(C(=O)O)cc21]

2-(2,5-Dichloro-phenyl)-4,4-dimethyl-1,2,3,4-tetrahydro-quinoline-6-carboxylic acid methyl ester To a stirred solution of 4-aminobenzoic acid methyl ester (1.5 g, 10 mmol) and 2,5-dichloro-benzaldehyde (1.8 g, 10 mmol) in MeCN (5 mL) were added isobutene (2.1 mL, 30 mmol) and ytterbium(III) trifluoromethanesulfonate (Yb(OTf)₃) (1.3 g, 2 mmol). The resulting mixture was stirred at 80° C. for 18 hours in sealed tube. The mixture was diluted with water (50 mL), extracted with diethyl ether (50 mL×3). The extracts were washed with water (100 mL) and brine (100 mL) and then dried over anhydrous Na₂SO₄. The solvent was removed in vacuo and the residue was purified by ISCO combi-flash chromatography (gradient elution, 0-10% ethyl acetate in petroleum ether) to 2-(2,5-dichloro-phenyl)-4,4-dimethyl-1,2,3,4-tetrahydro-quinoline-6-carboxylic acid methyl ester (1.8 g, 50%) as a light yellow solid (reference: Kiselyov, A. S. et al., *Tetrahedron* 54 (1998) 5089): MS (ESI⁺) [(M+H)⁺] 364.2.

2-(2,5-Dichloro-phenyl)-4,4-dimethyl-1,2,3,4-tetrahydro-quinoline-6-carboxylic acid To a solution of 2-(2,5-dichloro-phenyl)-4,4-dimethyl-1,2,3,4-tetrahydro-quinoline-6-carboxylic acid methyl ester (1.0 g, 2.8 mmol) in tetrahydrofuran (8 mL) and methanol (8 mL) was added 3N sodium hydroxide (5 mL). The reaction mixture was stirred at 80° C. for 4 hours, and then diluted with water (10 mL), extracted with diethyl ether (20 mL). The organic layer was discarded. The aqueous layer was acidified with concentrated hydrochloric acid to pH 4 and extracted with ethyl acetate (40 mL×3), and the combined organics were dried over anhydrous Na₂SO₄. The solvent was removed in vacuo and purified by preparative HPLC to afford 2-(2,5-dichloro-phenyl)-4,4-dimethyl-1,2,3,4-tetrahydro-quinoline-6-carboxylic acid (600 mg, 61.4%) as a yellow foam. MS (ESI⁺) [(M+H)⁺] 350.1.

Example 16

4,4-Dimethyl-2-(1-methyl-1-phenyl-ethyl)-1,2,3,4-tetrahydro-quinoline-6-carboxylic acid

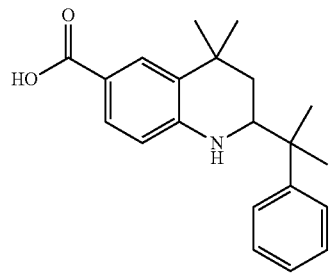 [SMILES: CC1(C)CC(C(C)(C)c2ccccc2)Nc2ccc(C(=O)O)cc21]

The title compound was prepared in analogy to example 15 starting from 2-methyl-2-phenyl-propionaldehyde. MS (ESI⁺) [(M+H)⁺] 324.1.

Example 17

7-Chloro-2-(5-chloro-2-fluoro-phenyl)-4,4-dimethyl-1,2,3,4-tetrahydro-quinoline-6-carboxylic acid

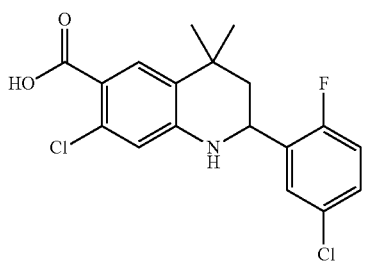 [SMILES: CC1(C)CC(c2cc(Cl)ccc2F)Nc2cc(Cl)c(C(=O)O)cc21]

The title compound was prepared in analogy to example 15 starting from 5-chloro-2-fluoro-benzaldehyde. MS (ESI⁺) [(M+H)⁺] 368.2.

Example 18

[2-(5-Chloro-2-fluoro-phenyl)-4,4-dimethyl-1,2,3,4-tetrahydro-quinolin-6-yl]-acetic acid

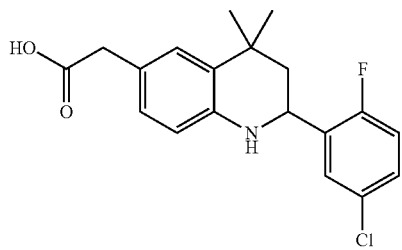 [SMILES: CC1(C)CC(c2cc(Cl)ccc2F)Nc2ccc(CC(=O)O)cc21]

The title compound was prepared in analogy to example 15 starting from 5-chloro-2-fluoro-benzaldehyde. MS (ESI$^+$) [(M+H)$^+$] 348.2.

Example 19

2-(3-Chloro-4-fluoro-phenyl)-4-methyl-4-vinyl-1,2,3,4-tetrahydro-quinoline-6-carboxylic acid

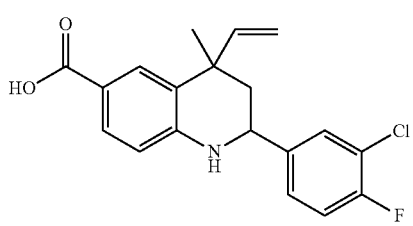 [SMILES: C=CC1(C)CC(c2ccc(F)c(Cl)c2)Nc2ccc(C(=O)O)cc21]

The title compound was prepared in analogy to example 15 starting from 3-chloro-4-fluoro-benzaldehyde. MS (ESI$^+$) [(M+H)$^+$] 346.2.

Example 20

2-(3-Chloro-4-fluoro-phenyl)-4-methyl-4-phenyl-1,2,3,4-tetrahydro-quinoline-6-carboxylic acid

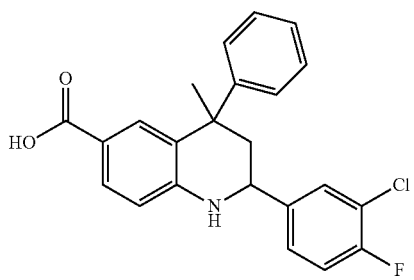 [SMILES: CC1(c2ccccc2)CC(c2ccc(F)c(Cl)c2)Nc2ccc(C(=O)O)cc21]

The title compound was prepared in analogy to example 15 starting from 3-chloro-4-fluoro-benzaldehyde. MS (ESI$^+$) [(M+H)$^+$] 396.2.

Example 21

2-(5-Fluoro-2-isopropoxy-phenyl)-4,4-dimethyl-1,2,3,4-tetrahydro-quinoline-6-carboxylic acid

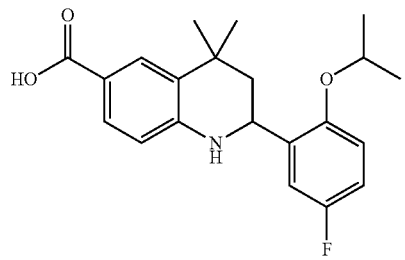 [SMILES: CC(C)Oc1ccc(F)cc1C1CC(C)(C)c2cc(C(=O)O)ccc2N1]

The title compound was prepared in analogy to example 15 starting from 5-fluoro-2-isopropoxy-benzaldehyde. MS (ESI$^+$) [(M+H)$^+$] 358.1.

Example 22

4,4-Dimethyl-2-(3-morpholin-4-yl-phenyl)-1,2,3,4-tetrahydro-quinoline-6-carboxylic acid

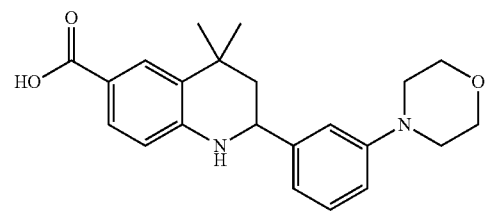 [SMILES: CC1(C)CC(c2cccc(N3CCOCC3)c2)Nc2ccc(C(=O)O)cc21]

4,4-Dimethyl-2-(3-morpholin-4-yl-phenyl)-1,2,3,4-tetrahydro-quinoline-6-carboxylic acid methyl ester The mixture of 4,4-dimethyl-2-(3-bromo-phenyl)-1,2,3,4-tetrahydro-quinoline-6-carboxylic acid methyl ester as prepared according to Example 1 (374 mg, 1 mmol), CuI (60 mg, 0.3 mmol), L-proline (70 mg, 0.6 mmol) and morpholine (440 mg, 5 mmol) in DMSO (5 mL) was stirred at 120° C. for 16 hours under a nitrogen atmosphere. The reaction mixture was diluted with water (20 mL), extracted with ethyl acetate (20 mL×3) and washed with brine (100 mL) and then dried over anhydrous Na$_2$SO$_4$. The solvent was removed in vacuo and the residue was purified by ISCO combi-flash chromatography (gradient elution, 30-60% ethyl acetate in petroleum ether) to afford 4,4-dimethyl-2-(3-morpholin-4-yl-phenyl)-1,2,3,4-tetrahydro-quinoline-6-carboxylic acid methyl ester (200 mg, 52.6%) as a white solid. MS (ESI$^+$) [(M+H)$^+$] 381.1.

4,4-Dimethyl-2-(3-morpholin-4-yl-phenyl)-1,2,3,4-tetrahydro-quinoline-6-carboxylic acid To a solution of 4,4-dimethyl-2-(3-morpholin-4-yl-phenyl)-1,2,3,4-tetrahydro-quinoline-6-carboxylic acid methyl ester (100 mg, 0.3 mmol) in tetrahydrofuran (2 mL) and methanol (2 mL) was added 3 N sodium hydroxide (1 mL). The reaction mixture was stirred at 80° C. for 6 hours, and then diluted with water (10 mL), extracted with diethyl ether (20 mL). The organic layer was discarded. The aqueous layer was acidified with concentrated hydrochloric acid to pH 4 and extracted with ethyl acetate (40 mL×3); and the combined organics were dried over anhydrous Na₂SO₄ The solvent was removed in vacuo and purified by preparative HPLC to afford 4,4-dimethyl-2-(3-morpholin-4-yl-phenyl)-1,2,3,4-tetrahydro-quinoline-6-carboxylic acid (50 mg, 52%) as a yellow foam. MS (ESI⁺) [(M+H)⁺] 367.2.

Example 23

2-[3-(4-Isopropyl-piperazin-1-yl)-phenyl]-4,4-dimethyl-1,2,3,4-tetrahydro-quinoline-6-carboxylic acid

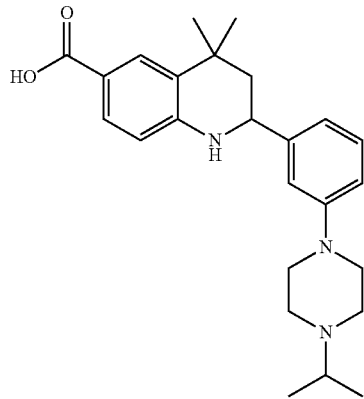 [SMILES: CC(C)N1CCN(c2cccc(C3CC(C)(C)c4cc(C(=O)O)ccc4N3)c2)CC1]

The title compound was prepared in analogy to example 22 starting from 2-(3-bromo-phenyl)-4,4-dimethyl-1,2,3,4-tetrahydro-quinoline-6-carboxylic acid methyl ester. MS (ESI⁺) [(M+H)⁺] 408.1.

Example 24

4,4-Dimethyl-2-(3-piperazin-1-yl-phenyl)-1,2,3,4-tetrahydro-quinoline-6-carboxylic acid

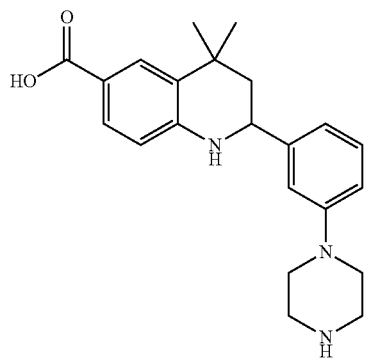 [SMILES: CC1(C)CC(c2cccc(N3CCNCC3)c2)Nc2ccc(C(=O)O)cc21]

The title compound was prepared in analogy to example 22 starting from 2-(3-bromo-phenyl)-4,4-dimethyl-1,2,3,4-tetrahydro-quinoline-6-carboxylic acid methyl ester. MS (ESI⁺) [(M+H)⁺] 366.1.

Example 25

6-(3-Chloro-4-fluoro-phenyl)-8-methyl-8-vinyl-5,6,7,8-tetrahydro-[1,5]naphthyridine-2-carboxylic acid

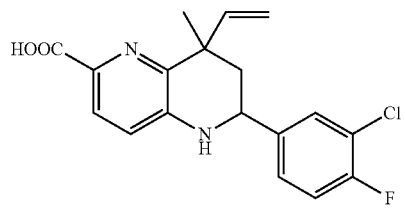 [SMILES: C=CC1(C)CC(c2ccc(F)c(Cl)c2)Nc2ccc(C(=O)O)nc21]

5-[(3-Chloro-4-fluoro-benzylidene)-amino]-pyridine-2-carbonitrile

A mixture of 5-amino-2-cyanopyridine (2.86 g, 24 mmol), 3-chloro-4-fluoro-benzaldehyde (3.79 g, 24 mmol) and p-toluenesulfonic acid (92 mg, 0.5 mmol) in toluene (150 mL) was heated to reflux for 12 hours. Then the reaction mixture was cooled to room temperature. The solvent was removed in vacuo and the residue was washed with ether to afford 5-[(3-chloro-4-fluoro-benzylidene)-amino]-pyridine-2-carbonitrile (5.8 g, 93.6%) as a light yellow solid. MS (ESI⁺) [(M+H)⁺] 260.1.

6-(3-Chloro-4-fluoro-phenyl)-8-methyl-8-vinyl-5,6,7,8-tetrahydro-[1,5]naphthyridine-2-carbonitrile To a stirred solution 5-[(3-chloro-4-fluoro-benzylidene)-amino]-pyridine-2-carbonitrile (3.7 g, 14.3 mmol) in MeCN (36 mL) were added isoprene (5.8 mL, 57.1 mol) and scandium(III) trifluoromethanesulfonate (Sc(OTf)₃) (1.4 g, 2.9 mmol). The resulting mixture was stirred at 80° C. for 16 hours in sealed tube. The mixture was extracted with diethyl ether (80 mL) and washed with water (100 mL) and brine (100 mL) and then dried over anhydrous Na₂SO₄. The solvent was removed in vacuo and the residue was purified by ISCO combi-flash chromatography (gradient elution, 0-20% ethyl acetate in petroleum ether) to afford 6-(3-chloro-4-fluoro-phenyl)-8-methyl-8-vinyl-5,6,7,8-tetrahydro-[1,5]naphthyridine-2-carbonitrile (0.25 g, 5.5%) as white powder. MS (ESI⁺) [(M+H)⁺] 328.2.

6-(3-Chloro-4-fluoro-phenyl)-8-methyl-8-vinyl-5,6,7,8-tetrahydro-[1,5]naphthyridine-2-carboxylic acid methyl ester 6-(3-chloro-4-fluoro-phenyl)-8-methyl-8-vinyl-5,6,7,8-tetrahydro-[1,5]naphthyridine-2-carbonitrile (327 mg, 1 mmol) was dissolved in MeOH (30 mL, saturated with HCl gas) and stirred at 75° C. overnight. The mixture was cooled to room temperature, poured into saturate NaHCO₃ solution (150 mL) carefully, and extracted with ethyl acetate (50 mL×3). The organic layers were washed with brine (10 mL), dried over anhydrous Na₂SO₄ and concentrated in vacuo. The residue was purified by ISCO combi-flash chromatography (gradient elution, 0-35% ethyl acetate in petroleum ether) to give 6-(3-chloro-4-fluoro-phenyl)-8-methyl-8-vinyl-5,6,7,8-tetrahydro-[1,5]naphthyridine-2-carboxylic acid methyl ester (310 mg, 86%) as a yellow solid. MS (ESI⁺) [(M+H)⁺] 361.2.

6-(3-Chloro-4-fluoro-phenyl)-8-methyl-8-vinyl-5,6,
7,8-tetrahydro-[1,5]naphthyridine-2-carboxylic acid To a solution of 6-(3-chloro-4-fluoro-phenyl)-8-methyl-8-vinyl-5,6,7,8-tetrahydro-[1,5]naphthyridine-2-carboxylic acid methyl ester (300 mg, 0.8 mmol) in tetrahydrofuran (2 mL) and methanol (2 mL) was added 3 N sodium hydroxide (1 mL). The reaction mixture was stirred at room temperature for 16 hours, and then diluted with water (10 mL), extracted with diethyl ether (20 mL). The organic layer was discarded. The aqueous layer was acidified with concentrated hydrochloric acid to pH 4 and extracted with ethyl acetate (40 mL×3), and the combined organics were dried over anhydrous $Na_2SO_4$. The solvent was removed in vacuo and purified by preparative HPLC to afford 6-(3-chloro-4-fluoro-phenyl)-8-methyl-8-vinyl-5,6,7,8-tetrahydro-[1,5] naphthyridine-2-carboxylic acid (180 mg, 62.7%) as a yellow oil. MS (ESI$^+$) [(M+H)$^+$] 347.2.

Example 26

6-(3-Chloro-4-fluoro-phenyl)-8-ethyl-8-methyl-5,6,
7,8-tetrahydro-[1,5]naphthyridine-2-carboxylic acid

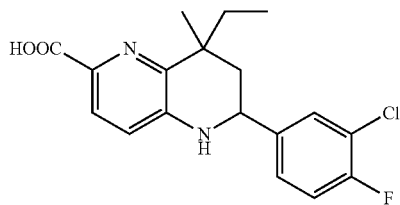 [SMILES: CCC1(C)CC(c2ccc(F)c(Cl)c2)Nc2ccc(C(=O)O)nc21]

The mixture solution of 6-(3-chloro-4-fluoro-phenyl)-8-methyl-8-vinyl-5,6,7,8-tetrahydro-[1,5]naphthyridine-2-carboxylic acid (100 mg, 0.3 mmol) and 10% palladium on active carbon (30 mg) in methanol (50 mL) was stirred at room temperature under hydrogen (14 psi) for 8 hours. The catalyst was filtered off and washed with ethyl acetate. The filtrate was concentrated in vacuo and purified by preparative HPLC to afford 6-(3-chloro-4-fluoro-phenyl)-8-ethyl-8-methyl-5,6,7,8-tetrahydro-[1,5]naphthyridine-2-carboxylic acid (30 mg, 30%) as a yellow oil. MS (ESI$^+$) [(M+H)$^+$] 349.2.

Example 27

6-(3-Chloro-4-fluoro-phenyl)-8-ethyl-8-methyl-5-(3-methyl-butyl)-5,6,7,8-tetrahydro-[1,5]naphthyridine-2-carboxylic acid

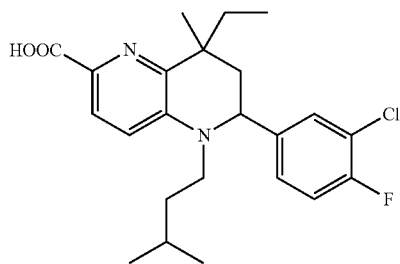 [SMILES: CCC1(C)CC(c2ccc(F)c(Cl)c2)N(CCC(C)C)c2ccc(C(=O)O)nc21]

6-(3-Chloro-4-fluoro-phenyl)-8-ethyl-8-methyl-5,6,
7,8-tetrahydro-[1,5]naphthyridine-2-carboxylic acid
methyl ester The mixture solution of 6-(3-chloro-4-fluoro-phenyl)-8-methyl-8-vinyl-5,6,7,8-tetrahydro-[1,5]naphthyridine-2-carboxylic acid methyl ester (360 mg, 1 mmol) and 10% palladium on active carbon (120 mg) in methanol (50 mL) was stirred at room temperature under hydrogen (14 psi) for 8 hours. The catalyst was filtered off and washed with ethyl acetate. The filtrate was concentrated in vacuo to afford 6-(3-chloro-4-fluoro-phenyl)-8-ethyl-8-methyl-5,6,7,8-tetrahydro-[1,5]naphthyridine-2-carboxylic acid methyl ester (360 mg, quant.) as a yellow oil. MS (ESI$^+$) [(M+H)$^+$] 363.2.

6-(3-Chloro-4-fluoro-phenyl)-8-ethyl-8-methyl-5-(3-methyl-butyl)-5,6,7,8-tetrahydro-[1,5]naphthyridine-2-carboxylic acid methyl ester To a 0° C. solution of 6-(3-chloro-4-fluoro-phenyl)-8-ethyl-8-methyl-5,6,7,8-tetrahydro-[1,5]naphthyridine-2-carboxylic acid methyl ester (200 mg, 0.5 mmol) in N,N-dimethylformamide (5 mL) was added a 60% dispersion of sodium hydride in mineral oil (44 mg, 1.1 mmol) portionwise. The mixture was stirred at 0° C. for 30 min and then 1-iodo-3-methyl-butane (327 mg, 1.6 mmol) was added to above mixture dropwise at 0° C. The mixture was stirred at 0° C. for 3 hours and then extracted with ethyl acetate, washed with brine, dried over anhydrous sodium sulfate and concentrated in vacuo. The yellowish residue was purified by ISCO combiflash chromatography (gradient elution, 0-5% ethyl acetate/hexane) to afford 6-(3-chloro-4-fluoro-phenyl)-8-ethyl-8-methyl-5-(3-methyl-butyl)-5,6,7,8-tetrahydro-[1,5]naphthyridine-2-carboxylic acid methyl ester (160 mg, 67.5%) as a yellow oil. MS (ESI$^+$) [(M+H)$^+$] 433.1.

6-(3-Chloro-4-fluoro-phenyl)-8-ethyl-8-methyl-5-(3-methyl-butyl)-5,6,7,8-tetrahydro-[1,5]naphthyridine-2-carboxylic acid To a solution of 6-(3-chloro-4-fluoro-phenyl)-8-ethyl-8-methyl-5-(3-methyl-butyl)-5,6,7,8-tetrahydro-[1,5]naphthyridine-2-carboxylic acid methyl ester (100 mg, 0.2 mmol) in tetrahydrofuran (2 mL) and methanol (2 mL) was added 3 N sodium hydroxide (1 mL). The reaction mixture was stirred at room temperature for 16 hours, and then diluted with water (10 mL), extracted with diethyl ether (20 mL). The organic layer was discarded. The aqueous layer was acidified with concentrated hydrochloric acid to pH 4 and extracted with ethyl acetate (40 mL×3), and the combined organics were dried over anhydrous $Na_2SO_4$. The solvent was removed in vacuo and purified by preparative HPLC to afford 6-(3-chloro-4-fluoro-phenyl)-8-ethyl-8-methyl-5-(3-methyl-butyl)-5,6,7,8-tetrahydro-[1,5]naphthyridine-2-carboxylic acid (30 mg, 31.3%) as a yellow oil. MS (ESI$^+$) [(M+H)$^+$] 419.1.

Example 28

2-(5-Fluoro-2-methyl-phenyl)-spiro(cyclopropane-1,4'-1',2',3',4'-tetrahydroquinoline)-6-carboxylic acid cyclobutylamide

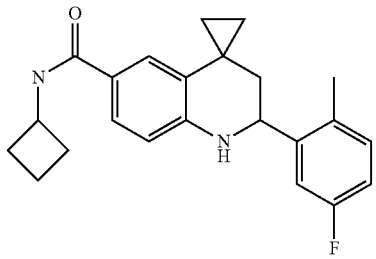 [SMILES: Cc1ccc(F)cc1C1CC2(CC2)c2cc(C(=O)NC3CCC3)ccc2N1]

A solution of 2-(5-fluoro-2-methyl-phenyl)-spiro(cyclopropane-1,4'-1',2',3',4'-tetrahydroquinoline)-6-carboxylic acid (311 mg, 1 mmol), cyclobutylamine (213 mg, 3 mmol), o-(7-azabenzotriazol-1-yl)-N,N,N',N'-tetramethyluronium hexafluorophosphate (HATU) (760 mg, 2 mmol) and N,N-diisopropyl ethylamine (386 mg, 3 mmol) in N,N-dimethyl-formamide (3 mL) was stirred at room temperature for 12 hours under a nitrogen atmosphere. Purification by preparative HPLC affords 2-(5-fluoro-2-methyl-phenyl)-spiro(cyclopropane-1,4'-1',2',3',4'-tetrahydroquinoline)-6-carboxylic acid cyclobutylamide (112 mg, 31.3%) as a yellow powder. (ESI$^+$) [(M+H)$^+$] 365.1.

Example 29

2-(5-Fluoro-2-methyl-phenyl)-spiro(cyclopropane-1,4'-1',2',3',4'-tetrahydroquinoline)-6-carboxylic acid dimethylamide

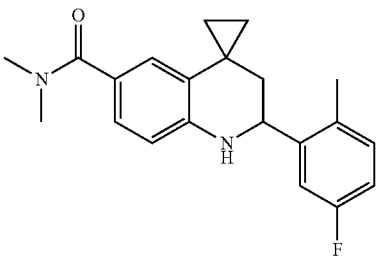 [SMILES: Cc1ccc(F)cc1C1CC2(CC2)c2cc(C(=O)N(C)C)ccc2N1]

The title compound was prepared in analogy to example 28 starting from 2-(5-fluoro-2-methyl-phenyl)-spiro(cyclopropane-1,4'-1',2',3',4'-tetrahydroquinoline)-6-carboxylic acid. MS (ESI$^+$) [(M+H)$^+$] 339.2.

Example 30

[2-(5-Fluoro-2-methyl-phenyl)-spiro(cyclopropane-1,4'-1',2',3',4'-tetrahydroquinolin)-6-yl]-morpholin-4-yl-methanone

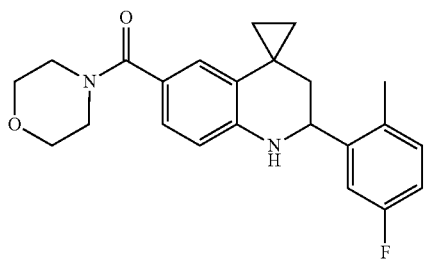 [SMILES: Cc1ccc(F)cc1C1CC2(CC2)c2cc(C(=O)N3CCOCC3)ccc2N1]

The title compound was prepared in analogy to example 28 starting from 2-(5-fluoro-2-methyl-phenyl)-spiro(cyclopropane-1,4'-1',2',3',4'-tetrahydroquinoline)-6-carboxylic acid. MS (ESI$^+$) [(M+H)$^+$] 381.2.

Example 31

[2-(5-Fluoro-2-methyl-phenyl)-spiro(cyclopropane-1,4'-1',2',3',4'-tetrahydroquinolin)-6-yl]-(4-methyl-piperazin-1-yl)-methanone

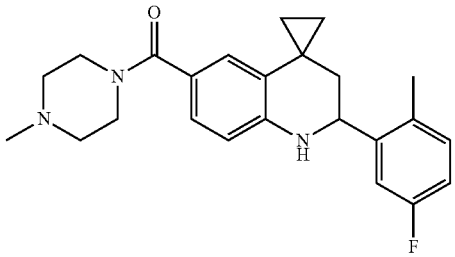 [SMILES: Cc1ccc(F)cc1C1CC2(CC2)c2cc(C(=O)N3CCN(C)CC3)ccc2N1]

The title compound was prepared in analogy to example 28 starting from 2-(5-fluoro-2-methyl-phenyl)-spiro(cyclopropane-1,4'-1',2',3',4'-tetrahydroquinoline)-6-carboxylic acid. MS. (ESI$^+$) [(M+H)$^+$] 394.2.

Example 32

[2-(2-Bromo-5-fluoro-phenyl)-spiro(cyclopropane-1,4'-1',2',3',4'-tetrahydroquinolin)-6-yl]-morpholin-4-yl-methanone

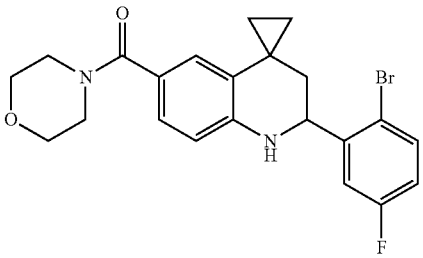

The title compound was prepared in analogy to example 28 starting from 2-(5-fluoro-2-bromo-phenyl)-spiro(cyclopropane-1,4'-1',2',3',4'-tetrahydroquinoline)-6-carboxylic acid. MS (ESI$^+$) [(M+H)$^+$] 445.2, 447.1.

Example 33

2-(2-Bromo-5-fluoro-phenyl)-spiro(cyclopropane-1,4'-1',2',3',4'-tetrahydroquinoline)-6-carboxylic acid isopropylamide

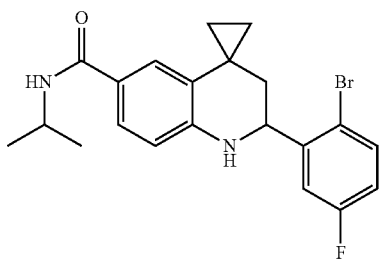 [SMILES: CC(C)NC(=O)c1ccc2c(c1)C1(CC1)CC(c1cc(F)ccc1Br)N2]

The title compound was prepared in analogy to example 28 starting from 2-(5-fluoro-2-bromo-phenyl)-spiro(cyclopro pane-1,4'-1',2',3',4'-tetrahydroquinoline)-6-carboxylic acid. MS (ESI⁺) [(M+H)⁺] 417.2, 419.1.

Example 34

2-(2-Bromo-5-fluoro-phenyl)-spiro(cyclopropane-1,4'-1',2',3',4'-tetrahydroquinoline)-6-carboxylic acid dimethylamide

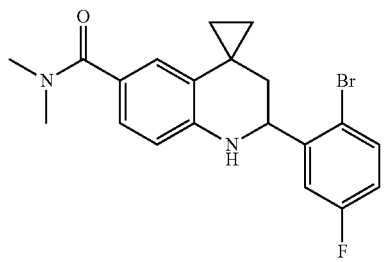 [SMILES: CN(C)C(=O)c1ccc2c(c1)C1(CC1)CC(c1cc(F)ccc1Br)N2]

The title compound was prepared in analogy to example 28 starting from 2-(5-fluoro-2-bromo-phenyl)-spiro(cyclopropane-1,4'-1',2',3',4'-tetrahydroquinoline)-6-carboxylic acid. MS (ESI⁺) [(M+H)⁺] 403.2, 405.1.

Example 35

2-(2-Bromo-5-fluoro-phenyl)-spiro(cyclopropane-1,4'-1',2',3',4'-tetrahydroquinoline)-6-carboxylic acid cyclobutylamide

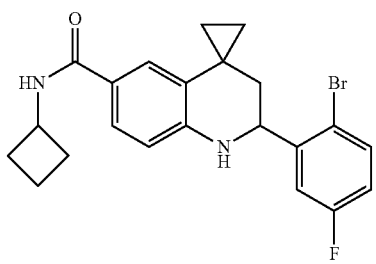 [SMILES: O=C(NC1CCC1)c1ccc2c(c1)C1(CC1)CC(c1cc(F)ccc1Br)N2]

The title compound was prepared in analogy to example 28 starting from 2-(5-fluoro-2-bromo-phenyl)-spiro(cyclopropane-1,4'-1',2',3',4'-tetrahydroquinoline)-6-carboxylic acid. MS (ESI⁺) [(M+H)⁺] 429.2, 431.1.

Example 36

2-(5-Bromo-2-fluoro-phenyl)-spiro(cyclopropane-1,4'-1',2',3',4'-tetrahydroquinoline)-6-carboxylic acid cyclobutylamide

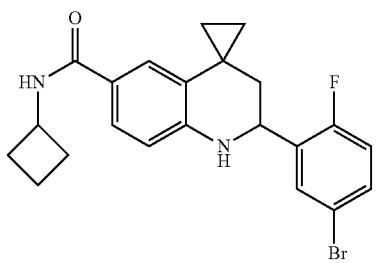 [SMILES: O=C(NC1CCC1)c1ccc2c(c1)C1(CC1)CC(c1cc(Br)ccc1F)N2]

The title compound was prepared in analogy to example 28 starting from 2-(5-bromo-2-fluoro-phenyl)-spiro(cyclopropane-1,4'-1',2',3',4'-tetrahydroquinoline)-6-carboxylic acid. MS (ESI⁺) [(M+H)⁺] 429.2, 431.1.

Example 37

2-(2,5-Dichloro-phenyl)-spiro(cyclopropane-1,4'-1',2',3',4'-tetrahydroquinoline)-6-carboxylic acid cyclopropylamide

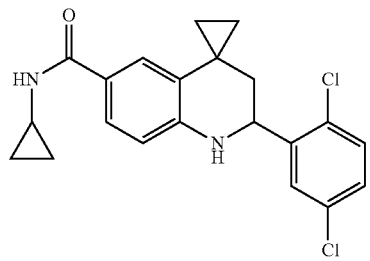 [SMILES: O=C(NC1CC1)c1ccc2c(c1)C1(CC1)CC(c1cc(Cl)ccc1Cl)N2]

The title compound was prepared in analogy to example 28 starting from 2-(2,5-dichloro-phenyl)-spiro(cyclopropane-1,4'-1',2',3',4'-tetrahydroquinoline)-6-carboxylic acid. MS. (ESI⁺) [(M+H)⁺] 387.2.

Example 38

2-(2,5-Dichloro-phenyl)-spiro(cyclopropane-1,4'-1',2',3',4'-tetrahydroquinoline)-6-carboxylic acid methylamide

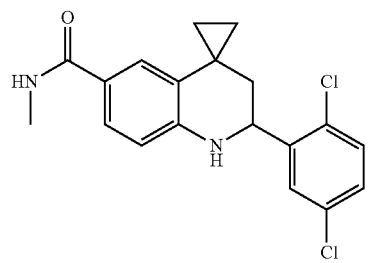 [SMILES: CNC(=O)c1ccc2c(c1)C1(CC1)CC(c1cc(Cl)ccc1Cl)N2]

The title compound was prepared in analogy to example 28 starting from 2-(2,5-dichloro-phenyl)-spiro(cyclopropane-1,4'-1',2',3',4'-tetrahydroquinoline)-6-carboxylic acid. MS (ESI⁺) [(M+H)⁺] 361.2.

Example 39

2-(2,5-Dichloro-phenyl)-spiro(cyclopropane-1,4'-1',2',3',4'-tetrahydroquinoline)-6-carboxylic acid cyclobutylamide

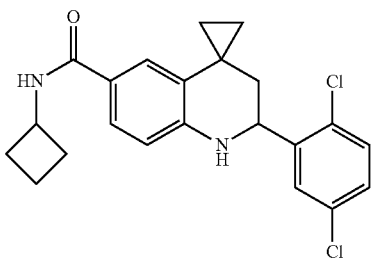 [SMILES: O=C(NC1CCC1)c1ccc2c(c1)C1(CC1)CC(c1cc(Cl)ccc1Cl)N2]

The title compound was prepared in analogy to example 28 starting from 2-(2,5-dichloro-phenyl)-spiro(cyclopropane-1, 4'-1',2',3',4'-tetrahydroquinoline)-6-carboxylic acid. MS (ESI⁺) [(M+H)⁺] 401.2.

Example 40

[2-(2,5-Dichloro-phenyl)-spiro(cyclopropane-1,4'-1', 2',3',4'-tetrahydroquinolin)-6-yl]-morpholin-4-yl-methanone

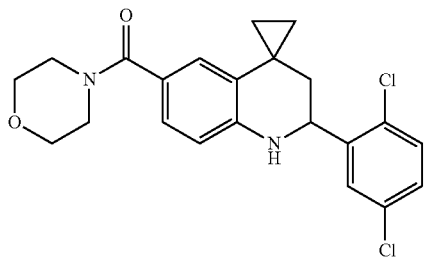 [SMILES: O=C(c1ccc2c(c1)C1(CC1)CC(c1cc(Cl)ccc1Cl)N2)N1CCOCC1]

The title compound was prepared in analogy to example 28 starting from 2-(2,5-dichloro-phenyl)-spiro(cyclopropane-1, 4'-1',2',3',4'-tetrahydroquinoline)-6-carboxylic acid. MS (ESI⁺) [(M+H)⁺] 417.2.

Example 41

2-(2,5-Dichloro-phenyl)-spiro(cyclopropane-1,4'-1', 2',3',4'-tetrahydroquinoline)-6-carboxylic acid iso-propylamide

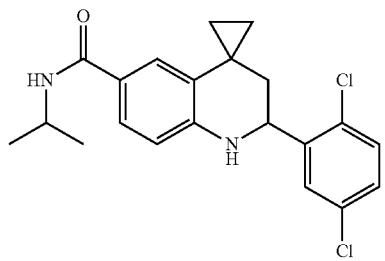 [SMILES: CC(C)NC(=O)c1ccc2c(c1)C1(CC1)CC(c1cc(Cl)ccc1Cl)N2]

The title compound was prepared in analogy to example 28 starting from 2-(2,5-dichloro-phenyl)-spiro(cyclopropane-1, 4'-1',2',3',4'-tetrahydroquinoline)-6-carboxylic acid. MS (ESI⁺) [(M+H)⁺] 389.2.

Example 42

[2-(2,5-Dichloro-phenyl)-spiro(cyclopropane-1,4'-1', 2',3',4'-tetrahydroquinolin)-6-yl]-(4-methanesulfo-nyl-piperazin-1-yl)-methanone

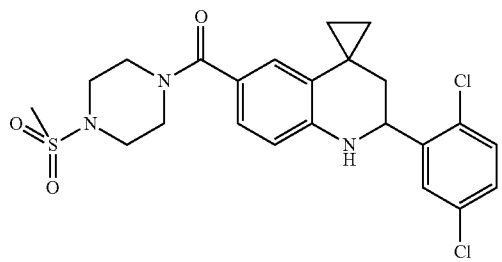 [SMILES: CS(=O)(=O)N1CCN(C(=O)c2ccc3c(c2)C2(CC2)CC(c2cc(Cl)ccc2Cl)N3)CC1]

The title compound was prepared in analogy to example 28 starting from 2-(2,5-dichloro-phenyl)-spiro(cyclopropane-1, 4'-1',2',3',4'-tetrahydroquinoline)-6-carboxylic acid. MS (ESI⁺) [(M+H)⁺] 494.2.

Example 43

2-(3,5-Dichloro-phenyl)-spiro(cyclopropane-1,4'-1', 2',3',4'-tetrahydroquinoline)-6-carboxylic acid cyclobutylamide

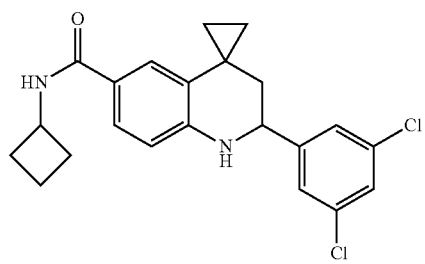 [SMILES: O=C(NC1CCC1)c1ccc2c(c1)C1(CC1)CC(c1cc(Cl)cc(Cl)c1)N2]

The title compound was prepared in analogy to example 28 starting from 2-(3,5-dichloro-phenyl)-spiro(cyclopropane-1, 4'-1',2',3',4'-tetrahydroquinoline)-6-carboxylic acid. MS (ESI⁺) [(M+H)⁺] 401.2.

Example 44

[2-(5-Chloro-2-fluoro-phenyl)-spiro(cyclopropane-1, 4'-1',2',3',4'-tetrahydroquinolin)-6-yl]-morpholin-4-yl-methanone

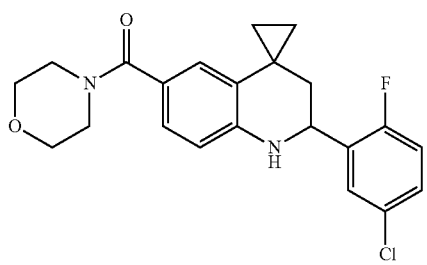 [SMILES: O=C(c1ccc2c(c1)C1(CC1)CC(c1cc(Cl)ccc1F)N2)N1CCOCC1]

The title compound was prepared in analogy to example 28 starting from 2-(5-chloro-2-fluoro-phenyl)-spiro(cyclopro-pane-1,4'-1',2',3',4'-tetrahydroquinoline)-6-carboxylic acid. MS (ESI⁺) [(M+H)⁺] 401.2.

Example 45

2-(5-Chloro-2-fluoro-phenyl)-spiro(cyclopropane-1, 4'-1',2',3',4'-tetrahydroquinoline)-6-carboxylic acid dimethylamide

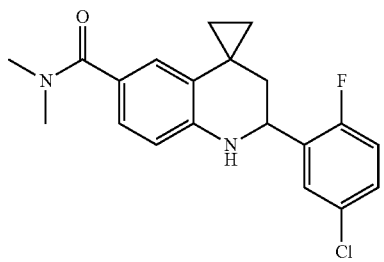 [SMILES: CN(C)C(=O)c1ccc2c(c1)C1(CC1)CC(c1cc(Cl)ccc1F)N2]

The title compound was prepared in analogy to example 28 starting from 2-(5-chloro-2-fluoro-phenyl)-spiro(cyclopropane-1,4'-1',2',3',4'-tetrahydroquinoline)-6-carboxylic acid. MS (ESI⁺) [(M+H)⁺] 359.1.

Example 46

2-(5-Chloro-2-fluoro-phenyl)-spiro(cyclopropane-1,4'-1',2',3',4'-tetrahydroquinoline)-6-carboxylic acid cyclobutylamide

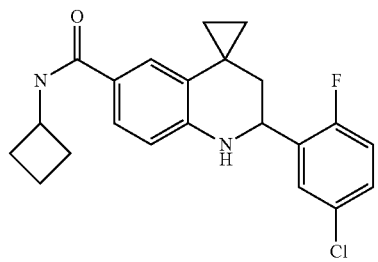

The title compound was prepared in analogy to example 28 starting from 2-(5-chloro-2-fluoro-phenyl)-spiro(cyclopropane-1,4'-1',2',3',4'-tetrahydroquinoline)-6-carboxylic acid. MS (ESI⁺) [(M+H)⁺] 385.3.

Example 47

2-(5-Chloro-2-fluoro-phenyl)-spiro(cyclopropane-1,4'-1',2',3',4'-tetrahydroquinoline)-6-carboxylic acid isopropylamide

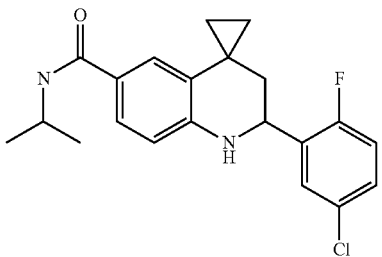 [SMILES: CC(C)NC(=O)c1ccc2c(c1)C1(CC1)CC(c1cc(Cl)ccc1F)N2]

The title compound was prepared in analogy to example 28 starting from 2-(5-chloro-2-fluoro-phenyl)-spiro(cyclopropane-1,4'-1',2',3',4'-tetrahydroquinoline)-6-carboxylic acid. MS (ESI⁺) [(M+H)⁺] 373.2.

Example 48

2-(2-Bromo-5-fluoro-phenyl)-spiro(cyclopropane-1,4'-1',2',3',4'-tetrahydroquinolin)-6-yl]-piperazin-1-yl-methanone

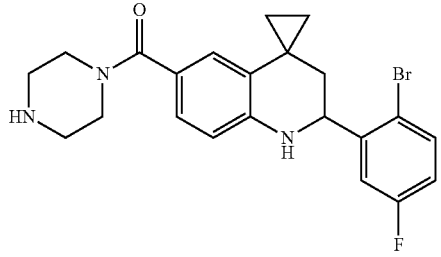 [SMILES: O=C(c1ccc2c(c1)C1(CC1)CC(c1cc(F)ccc1Br)N2)N1CCNCC1]

The title compound was prepared in analogy to example 28 starting from 2-(2-bromo-5-fluoro-phenyl)-spiro(cyclopropane-1,4'-1',2',3',4'-tetrahydroquinoline)-6-carboxylic acid. MS (ESI⁺) [(M+H)⁺] 444.1, 446.1.

Example 49

2-(2-Bromo-4-fluoro-6-methyl-phenyl)-spiro(cyclopropane-1,4'-1',2',3',4'-tetrahydroquinoline)-6-carboxylic acid methylamide

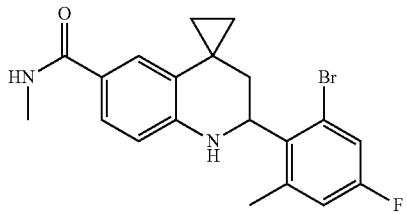 [SMILES: CNC(=O)c1ccc2c(c1)C1(CC1)CC(c1c(C)cc(F)cc1Br)N2]

The title compound was prepared in analogy to example 28 starting from 2-(2-bromo-4-fluoro-6-methyl-phenyl)-spiro(cyclopropane-1,4'-1',2',3',4'-tetrahydroquinoline)-6-carboxylic acid. MS (ESI⁺) [(M+H)⁺] 403.0, 405.0.

Example 50

4,4-Dimethyl-2-(1-methyl-1-phenyl-ethyl)-1,2,3,4-tetrahydro-quinoline-6-carboxylic acid dimethylamide

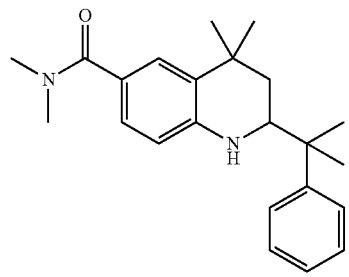 [SMILES: CN(C)C(=O)c1ccc2c(c1)C(C)(C)CC(C(C)(C)c1ccccc1)N2]

The title compound was prepared in analogy to example 28 starting from 4,4-dimethyl-2-(1-methyl-1-phenyl-ethyl)-1,2,3,4-tetrahydro-quinoline-6-carboxylic acid. MS (ESI⁺) [(M+H)⁺] 351.2.

Example 51

2-(2-Bromo-5-fluoro-phenyl)-spiro(cyclopentane-1,4'-1',2',3',4'-tetrahydroquinoline)-6-carboxylic acid dimethylamide

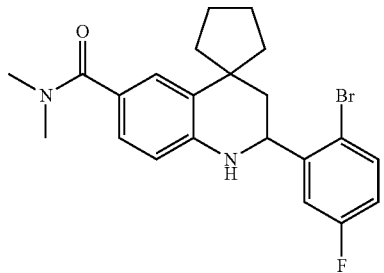 [SMILES: CN(C)C(=O)c1ccc2c(c1)C1(CCCC1)CC(c1cc(F)ccc1Br)N2]

The title compound was prepared in analogy to example 28 starting from 2-(2-bromo-5-fluoro-phenyl)-spiro(cyclopentane-1,4'-1',2',3',4'-tetrahydroquinoline)-6-carboxylic acid. MS (ESI⁺) [(M+H)⁺] 431.0, 433.0.

Example 52

2-(2-Bromo-5-fluoro-phenyl)-spiro(cyclopentane-1,4'-1',2',3',4'-tetrahydroquinoline)-6-carboxylic acid cyclopropylamide

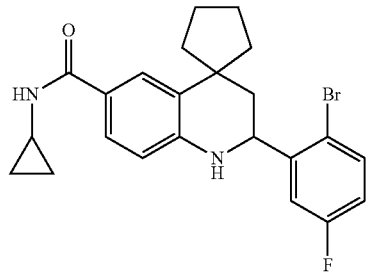 [SMILES: O=C(NC1CC1)c1ccc2c(c1)C1(CCCC1)CC(c1cc(F)ccc1Br)N2]

The title compound was prepared in analogy to example 28 starting from 2-(2-bromo-5-fluoro-phenyl)-spiro(cyclopentane-1,4'-1',2',3',4'-tetrahydroquinoline)-6-carboxylic acid. MS. (ESI⁺) [(M+H)⁺] 443.0, 445.0.

Example 53

2-(2-Bromo-5-fluoro-phenyl)-spiro(cyclopentane-1,4'-1',2',3',4'-tetrahydroquinoline)-6-carboxylic acid (1-methyl-piperidin-4-yl)-amide

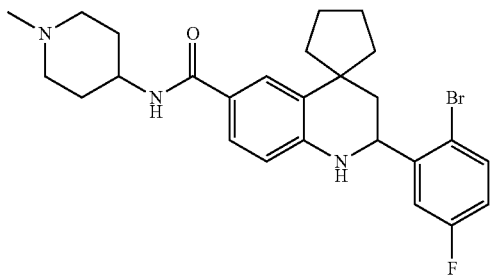 [SMILES: CN1CCC(NC(=O)c2ccc3c(c2)C2(CCCC2)CC(c2cc(F)ccc2Br)N3)CC1]

The title compound was prepared in analogy to example 28 starting from 2-(2-bromo-5-fluoro-phenyl)-spiro(cyclopentane-1,4'-1',2',3',4'-tetrahydroquinoline)-6-carboxylic acid. MS (ESI⁺) [(M+H)⁺] 500.1, 502.1.

Example 54

2-(2-Bromo-5-fluoro-phenyl)-spiro(cyclopentane-1,4'-1',2',3',4'-tetrahydroquinoline)-6-carboxylic acid cyclobutylamide

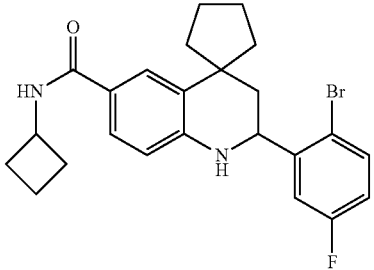 [SMILES: O=C(NC1CCC1)c1ccc2c(c1)C1(CCCC1)CC(c1cc(F)ccc1Br)N2]

The title compound was prepared in analogy to example 28 starting from 2-(2-bromo-5-fluoro-phenyl)-spiro(cyclopentane-1,4'-1',2',3',4'-tetrahydroquinoline)-6-carboxylic acid. MS (ESI⁺) [(M+H)⁺] 457.0, 459.0.

Example 55

2-(2-Bromo-5-fluoro-phenyl)-spiro(cyclopentane-1,4'-1',2',3',4'-tetrahydroquinoline)-6-carboxylic acid methylamide

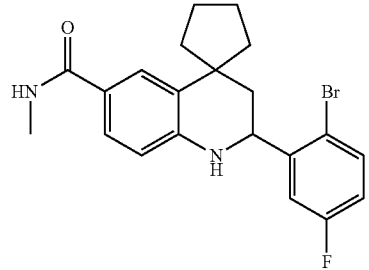 [SMILES: CNC(=O)c1ccc2c(c1)C1(CCCC1)CC(c1cc(F)ccc1Br)N2]

The title compound was prepared in analogy to example 28 starting from 2-(2-bromo-5-fluoro-phenyl)-spiro(cyclopentane-1,4'-1',2',3',4'-tetrahydroquinoline)-6-carboxylic acid. MS (ESI⁺) [(M+H)⁺] 417.0, 419.0.

Example 56

2-(2-Bromo-5-fluoro-phenyl)-spiro(cyclopentane-1,4'-1',2',3',4'-tetrahydroquinoline)-6-carboxylic acid (2-hydroxy-ethyl)-amide

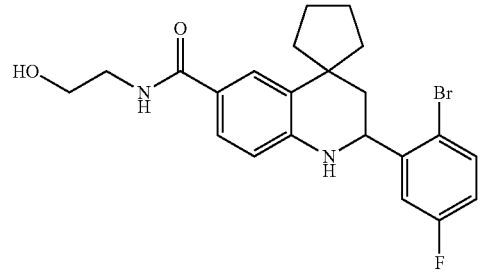 [SMILES: O=C(NCCO)c1ccc2c(c1)C1(CCCC1)CC(c1cc(F)ccc1Br)N2]

The title compound was prepared in analogy to example 28 starting from 2-(2-bromo-5-fluoro-phenyl)-spiro(cyclopentane-1,4'-1',2',3',4'-tetrahydroquinoline)-6-carboxylic acid. MS (ESI⁺) [(M+H)⁺] 447.0, 449.0.

Example 57

[2-(2-Bromo-5-fluoro-phenyl)-spiro(cyclopentane-1,4'-1',2',3',4'-tetrahydroquinolin)-6-yl]-morpholin-4-yl-methanone

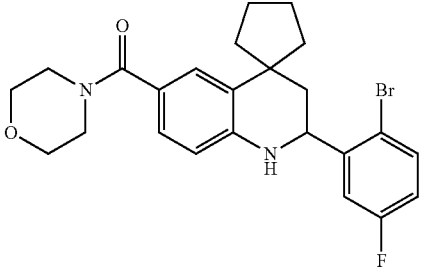 [SMILES: O=C(c1ccc2c(c1)C1(CCCC1)CC(c1cc(F)ccc1Br)N2)N1CCOCC1]

The title compound was prepared in analogy to example 28 starting from 2-(2-bromo-5-fluoro-phenyl)-spiro(cyclopentane-1,4'-1',2',3',4'-tetrahydroquinoline)-6-carboxylic acid. MS (ESI⁺) [(M+H)⁺] 473.0, 475.0.

Example 58

[2-(2-Bromo-5-fluoro-phenyl)-spiro(cyclopentane-1, 4'-1',2',3',4'-tetrahydroquinolin)-6-yl]-(4-methyl-piperazin-1-yl)-methanone

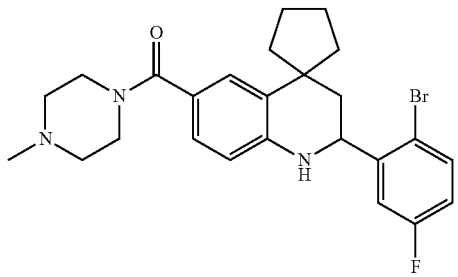 [SMILES: CN1CCN(C(=O)c2ccc3c(c2)C2(CCCC2)CC(c2cc(F)ccc2Br)N3)CC1]

The title compound was prepared in analogy to example 28 starting from 2-(2-bromo-5-fluoro-phenyl)-spiro(cyclopentane-1,4'-1',2',3',4'-tetrahydroquinoline)-6-carboxylic acid. MS (ESI⁺) [(M+H)⁺] 486.0, 488.0.

Example 59

2-(2-Bromo-5-fluoro-phenyl)-spiro(cyclopentane-1, 4'-1',2',3',4'-tetrahydroquinoline)-6-carboxylic acid oxetan-3-ylamide

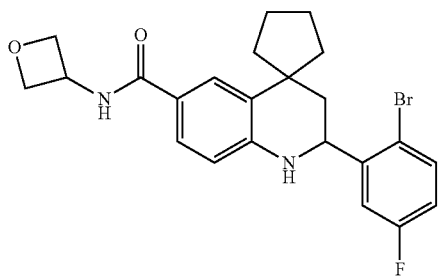 [SMILES: O=C(NC1COC1)c1ccc2c(c1)C1(CCCC1)CC(c1cc(F)ccc1Br)N2]

The title compound was prepared in analogy to example 28 starting from 2-(2-bromo-5-fluoro-phenyl)-spiro(cyclopentane-1,4'-1',2',3',4'-tetrahydroquinoline)-6-carboxylic acid. MS (ESI⁺) [(M+H)⁺] 459.0, 461.0.

Example 60

2-(2-Bromo-5-fluoro-phenyl)-spiro(cyclopentane-1, 4'-1',2',3',4'-tetrahydroquinoline)-6-carboxylic acid isopropylamide

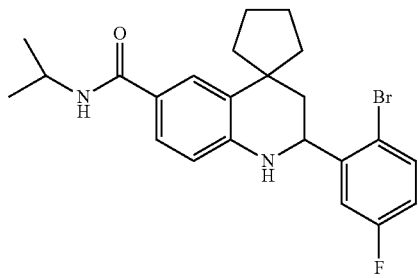 [SMILES: CC(C)NC(=O)c1ccc2c(c1)C1(CCCC1)CC(c1cc(F)ccc1Br)N2]

The title compound was prepared in analogy to example 28 starting from 2-(2-bromo-5-fluoro-phenyl)-spiro(cyclopentane-1,4'-1',2',3',4'-tetrahydroquinoline)-6-carboxylic acid. MS (ESI⁺) [(M+H)⁺] 445.0, 447.0.

Example 61

2-(2,5-Dichloro-phenyl)-spiro(cyclopentane-1,4'-1', 2',3',4'-tetrahydroquinoline)-6-carboxylic acid cyclobutylamide

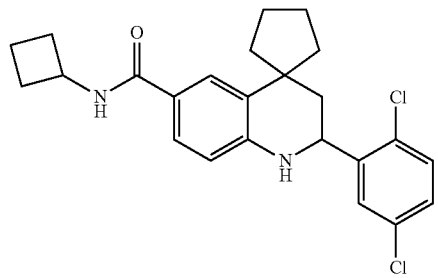

The title compound was prepared in analogy to example 28 starting from 2-(2,5-dichloro-phenyl)-spiro(cyclopentane-1, 4'-1',2',3',4'-tetrahydroquinoline)-6-carboxylic acid. MS (ESI⁺) [(M+H)⁺] 429.1.

Example 62

2-(3-Fluoro-phenyl)-spiro(cyclopentane-1,4'-1',2',3', 4'-tetrahydroquinoline)-6-carboxylic acid cyclobutylamide

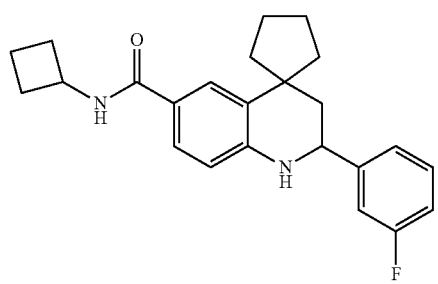 [SMILES: O=C(NC1CCC1)c1ccc2c(c1)C1(CCCC1)CC(c1cccc(F)c1)N2]

The title compound was prepared in analogy to example 28 starting from 2-(3-fluoro-phenyl)-spiro(cyclopentane-1,4'-1',2',3',4'-tetrahydroquinoline)-6-carboxylic acid. MS (ESI⁺) [(M+H)⁺] 379.2.

Example 63

2-(3-Morpholin-4-yl-phenyl)-spiro(cyclopentane-1, 4'-1',2',3',4'-tetrahydroquinoline)-6-carboxylic acid methylamide

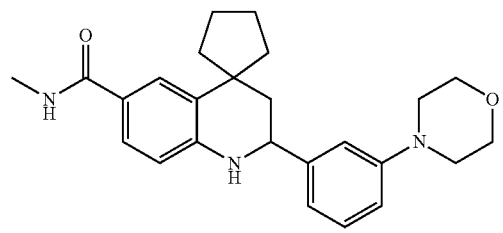 [SMILES: CNC(=O)c1ccc2c(c1)C1(CCCC1)CC(c1cccc(N3CCOCC3)c1)N2]

The title compound was prepared in analogy to example 28 starting from 2-(3-morpholin-4-yl-phenyl)-spiro(cyclopentane-1,4'-1',2',3',4'-tetrahydroquinoline)-6-carboxylic acid. MS (ESI⁺) [(M+H)⁺] 406.1.

Example 64

2-(5-Chloro-2-fluoro-phenyl)-spiro(cyclopentane-1,4'-1',2',3',4'-tetrahydroquinoline)-6-carboxylic acid cyclobutylamide

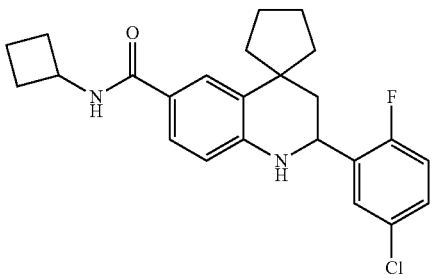 [SMILES: O=C(NC1CCC1)c1ccc2c(c1)C1(CCCC1)CC(c1cc(Cl)ccc1F)N2]

The title compound was prepared in analogy to example 28 starting from 2-(5-chloro-2-fluoro-phenyl)-spiro(cyclopentane-1,4'-1',2',3',4'-tetrahydroquinoline)-6-carboxylic acid. MS (ESI⁺) [(M+H)⁺] 413.3.

Example 65

2-(5-Chloro-2-fluoro-phenyl)-spiro(cyclopentane-1,4'-1',2',3',4'-tetrahydroquinoline)-6-carboxylic acid dimethylamide

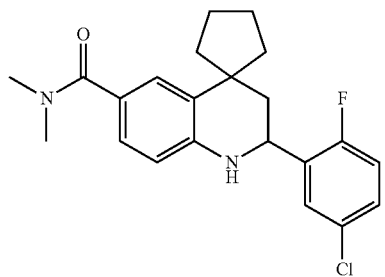 [SMILES: CN(C)C(=O)c1ccc2c(c1)C1(CCCC1)CC(c1cc(Cl)ccc1F)N2]

The title compound was prepared in analogy to example 28 starting from 2-(5-chloro-2-fluoro-phenyl)-spiro(cyclopentane-1,4'-1',2',3',4'-tetrahydroquinoline)-6-carboxylic acid. MS (ESI⁺) [(M+H)⁺] 387.1.

Example 66

2-(2,5-Dichloro-phenyl)-4,4-dimethyl-1,2,3,4-tetrahydro-quinoline-6-carboxylic acid cyclobutylamide

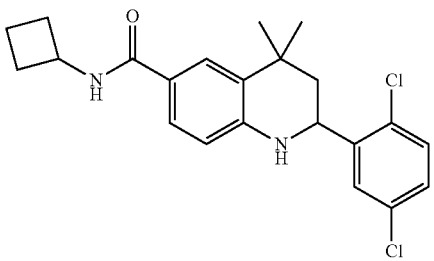 [SMILES: CC1(C)CC(c2cc(Cl)ccc2Cl)Nc2ccc(C(=O)NC3CCC3)cc21]

The title compound was prepared in analogy to example 28 starting from 2-(2,5-dichloro-phenyl)-4,4-dimethyl-1,2,3,4-tetrahydro-quinoline-6-carboxylic acid. MS (ESI⁺) [(M+H)⁺] 403.3.

Example 67

2-(5-Chloro-2-fluoro-phenyl)-4,4-dimethyl-1,2,3,4-tetrahydro-quinoline-6-carboxylic acid cyclobutylamide

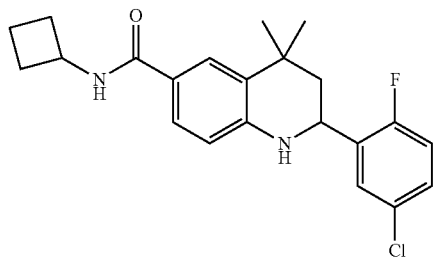 [SMILES: CC1(C)CC(c2cc(Cl)ccc2F)Nc2ccc(C(=O)NC3CCC3)cc21]

The title compound was prepared in analogy to example 28 starting from 2-(5-chloro-2-fluoro-phenyl)-4,4-dimethyl-1,2,3,4-tetrahydro-quinoline-6-carboxylic acid. MS (ESI⁺) [(M+H)⁺] 387.2.

Example 68

4,4-Dimethyl-2-(3-morpholin-4-yl-phenyl)-1,2,3,4-tetrahydro-quinoline-6-carboxylic acid (2-hydroxy-1-hydroxymethyl-1-methyl-ethyl)-amide

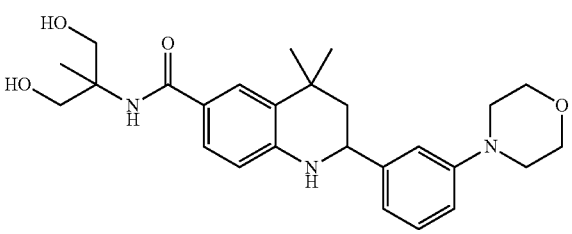 [SMILES: CC(CO)(CO)NC(=O)c1ccc2c(c1)C(C)(C)CC(c1cccc(N3CCOCC3)c1)N2]

The title compound was prepared in analogy to example 28 starting from 4,4-dimethyl-2-(3-morpholin-4-yl-phenyl)-1,2,3,4-tetrahydro-quinoline-6-carboxylic acid. MS (ESI⁺) [(M+H)⁺] 454.1.

Example 69

2-(3-Chloro-4-fluoro-phenyl)-spiro(cyclopentane-1,4'-1',2',3',4'-tetrahydroquinoline)-6-carboxylic acid cyclobutylamide

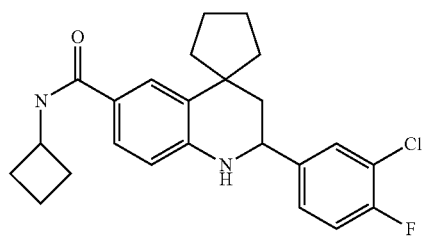 [SMILES: O=C(NC1CCC1)c1ccc2c(c1)C1(CCCC1)CC(c1ccc(F)c(Cl)c1)N2]

The title compound was prepared in analogy to example 28 starting from 2-(3-chloro-4-fluoro-phenyl)-spiro(cyclopentane-1,4'-1',2',3',4'-tetrahydroquinoline)-6-carboxylic acid. MS (ESI+) [(M+H)+] 413.3.

Example 70

6-(3-Chloro-4-fluoro-phenyl)-8-ethyl-8-methyl-5,6,7,8-tetrahydro-[1,5]naphthyridine-2-carboxylic acid cyclobutylamide

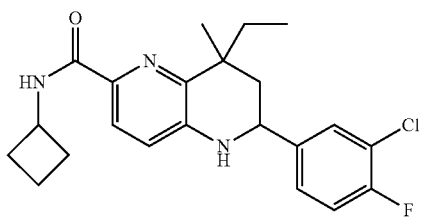 [SMILES: CCC1(C)CC(c2ccc(F)c(Cl)c2)Nc2ccc(C(=O)NC3CCC3)nc21]

The title compound was prepared in analogy to example 28 starting from 6-(3-chloro-4-fluoro-phenyl)-8-ethyl-8-methyl-5,6,7,8-tetrahydro-[1,5]naphthyridine-2-carboxylic acid. MS (ESI+) [(M+H)+] 402.1.

Example 71

4,4-Dimethyl-2-(3-morpholin-4-yl-phenyl)-1,2,3,4-tetrahydro-quinoline-6-carboxylic acid isopropylamide

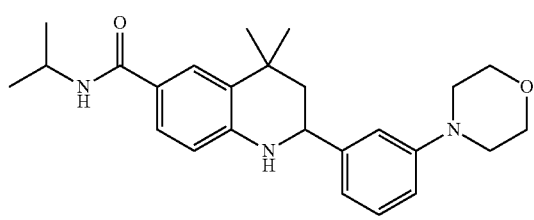 [SMILES: CC(C)NC(=O)c1ccc2c(c1)C(C)(C)CC(c1cccc(N3CCOCC3)c1)N2]

The title compound was prepared in analogy to example 28 starting from 4,4-dimethyl-2-(3-morpholin-4-yl-phenyl)-1,2,3,4-tetrahydro-quinoline-6-carboxylic acid. MS (ESI+) [(M+H)+] 408.2.

Example 72

N-[2-(1,1-dioxidothiomorpholin-4-yl)ethyl]-4,4-dimethyl-2-[3-(morpholin-4-yl)phenyl]-1,2,3,4-tetrahydroquinoline-6-carboxamide

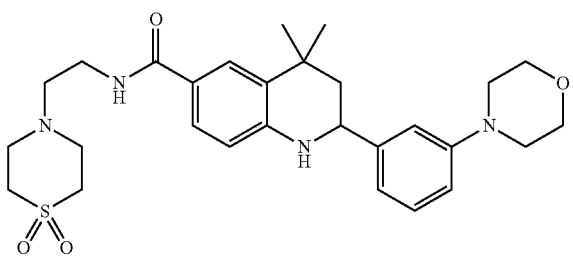 [SMILES: CC1(C)CC(c2cccc(N3CCOCC3)c2)Nc2ccc(C(=O)NCCN3CCS(=O)(=O)CC3)cc21]

The title compound was prepared in analogy to example 28 starting from 4,4-dimethyl-2-(3-morpholin-4-yl-phenyl)-1,2,3,4-tetrahydro-quinoline-6-carboxylic acid. MS (ESI+) [(M+H)+] 527.1.

Example 73

4,4-Dimethyl-2-(3-morpholin-4-yl-phenyl)-1,2,3,4-tetrahydro-quinoline-6-carboxylic acid (2,3-dihydroxy-propyl)-amide

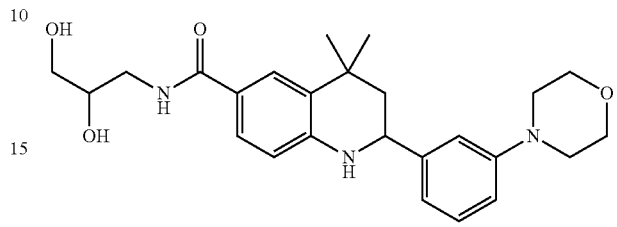

The title compound was prepared in analogy to example 28 starting from 4,4-dimethyl-2-(3-morpholin-4-yl-phenyl)-1,2,3,4-tetrahydro-quinoline-6-carboxylic acid. MS (ESI+) [(M+H)+] 440.1.

Example 74

N-[2-(1,1-dioxidothiomorpholin-4-yl)ethyl]-4,4-dimethyl-2-{3-[4-(propan-2-yl)piperazin-1-yl]phenyl}-1,2,3,4-tetrahydroquinoline-6-carboxamide

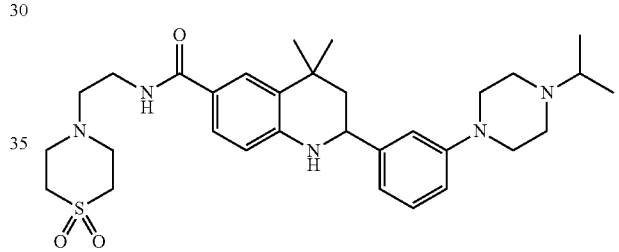

The title compound was prepared in analogy to example 28 starting from 2-[3-(4-isopropyl-piperazin-1-yl)-phenyl]-4,4-dimethyl-1,2,3,4-tetrahydro-quinoline-6-carboxylic acid. MS (ESI+) [(M+H)+] 568.1.

Example 75

N-[2-(1,1-dioxidothiomorpholin-4-yl)ethyl]-4,4-dimethyl-2-(2-phenylpropan-2-yl)-1,2,3,4-tetrahydroquinoline-6-carboxamide

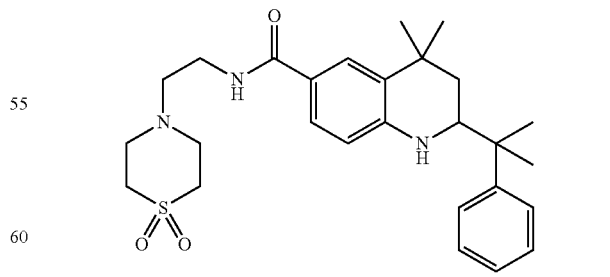

The title compound was prepared in analogy to example 28 starting from 4,4-dimethyl-2-(1-methyl-1-phenyl-ethyl)-1,2,3,4-tetrahydro-quinoline-6-carboxylic acid. MS (ESI+) [(M+H)+] 484.3.

Example 76

[4,4-Dimethyl-2-(1-methyl-1-phenyl-ethyl)-1,2,3,4-tetrahydro-quinolin-6-yl]-morpholin-4-yl-methanone

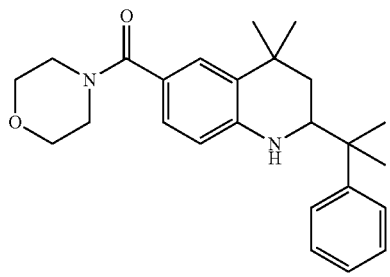 [SMILES: CC1(C)CC(C(C)(C)c2ccccc2)Nc2ccc(C(=O)N3CCOCC3)cc21]

The title compound was prepared in analogy to example 28 starting from 4,4-dimethyl-2-(1-methyl-1-phenyl-ethyl)-1,2,3,4-tetrahydro-quinoline-6-carboxylic acid. MS (ESI$^+$) [(M+H)$^+$] 393.1.

Example 77

[4,4-Dimethyl-2-(3-morpholin-4-yl-phenyl)-1,2,3,4-tetrahydro-quinolin-6-yl]-(3-hydroxy-3-methyl-pyrrolidin-1-yl)-methanone

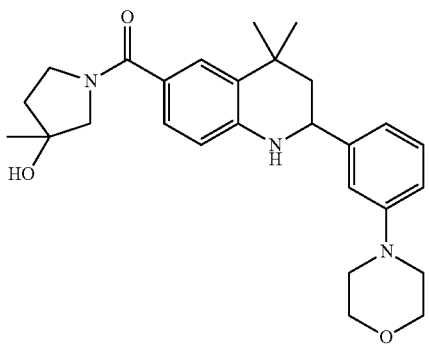 [SMILES: CC1(O)CCN(C(=O)c2ccc3c(c2)C(C)(C)CC(c2cccc(N4CCOCC4)c2)N3)C1]

The title compound was prepared in analogy to example 28 starting from 4,4-dimethyl-2-(3-morpholin-4-yl-phenyl)-1,2,3,4-tetrahydro-quinoline-6-carboxylic acid. MS (ESI$^+$) [(M+H)$^+$] 450.1.

Example 78

4,4-Dimethyl-2-(3-morpholin-4-yl-phenyl)-1,2,3,4-tetrahydro-quinoline-6-carboxylic acid (2-hydroxy-1-hydroxymethyl-ethyl)-amide

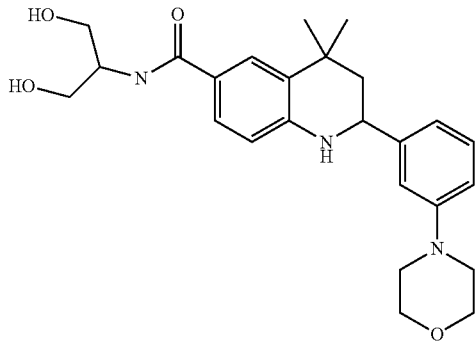 [SMILES: CC1(C)CC(c2cccc(N3CCOCC3)c2)Nc2ccc(C(=O)NC(CO)CO)cc21]

The title compound was prepared in analogy to example 28 starting from 4,4-dimethyl-2-(3-morpholin-4-yl-phenyl)-1,2,3,4-tetrahydro-quinoline-6-carboxylic acid. MS (ESI$^+$) [(M+H)$^+$] 440.2.

Example 79

4,4-Dimethyl-2-(3-morpholin-4-yl-phenyl)-1,2,3,4-tetrahydro-quinoline-6-carboxylic acid (2-hydroxy-ethyl)-amide

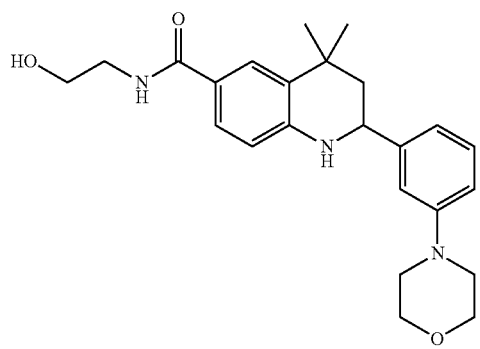 [SMILES: CC1(C)CC(c2cccc(N3CCOCC3)c2)Nc2ccc(C(=O)NCCO)cc21]

The title compound was prepared in analogy to example 28 starting from 4,4-dimethyl-2-(3-morpholin-4-yl-phenyl)-1,2,3,4-tetrahydro-quinoline-6-carboxylic acid. MS (ESI$^+$) [(M+H)$^+$] 410.1.

Example 80

[2-(3-Fluoro-5-morpholin-4-yl-phenyl)-4,4-dimethyl-1,2,3,4-tetrahydro-quinolin-6-yl]-(3-hydroxy-3-methyl-pyrrolidin-1-yl)-methanone

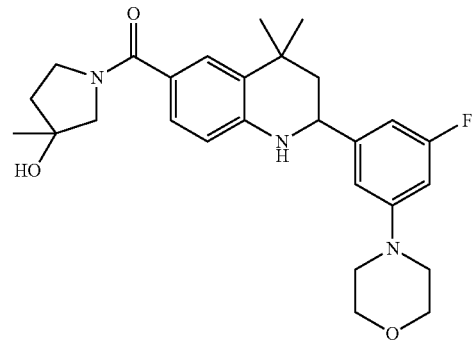 [SMILES: CC1(O)CCN(C(=O)c2ccc3c(c2)C(C)(C)CC(c2cc(F)cc(N4CCOCC4)c2)N3)C1]

The title compound was prepared in analogy to example 28 starting from 2-(3-fluoro-5-morpholin-4-yl-phenyl)-4,4-dimethyl-1,2,3,4-tetrahydro-quinoline-6-carboxylic acid. MS (ESI$^+$) [(M+H)$^+$] 468.3.

Example 81

[2-(3-Fluoro-5-morpholin-4-yl-phenyl)-4,4-dimethyl-1,2,3,4-tetrahydro-quinolin-6-yl]-morpholin-4-yl-methanone

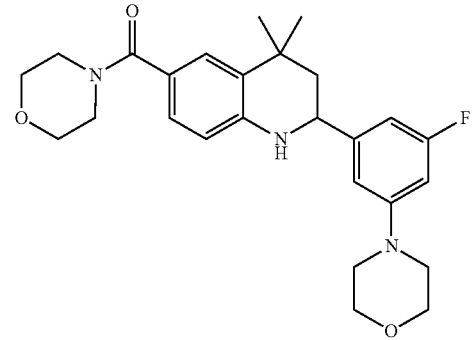 [SMILES: CC1(C)CC(c2cc(F)cc(N3CCOCC3)c2)Nc2ccc(C(=O)N3CCOCC3)cc21]

The title compound was prepared in analogy to example 28 starting from 2-(3-fluoro-5-morpholin-4-yl-phenyl)-4,4-dimethyl-1,2,3,4-tetrahydro-quinoline-6-carboxylic acid. MS (ESI+) [(M+H)+] 454.2.

Example 82

[4,4-Dimethyl-2-(3-morpholin-4-yl-phenyl)-1,2,3,4-tetrahydro-quinolin-6-yl]-morpholin-4-yl-methanone

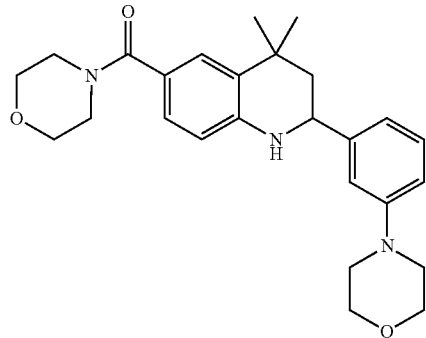 [SMILES: CC1(C)CC(c2cccc(N3CCOCC3)c2)Nc2ccc(C(=O)N3CCOCC3)cc21]

The title compound was prepared in analogy to example 28 starting from 4,4-dimethyl-2-(3-morpholin-4-yl-phenyl)-1,2,3,4-tetrahydro-quinoline-6-carboxylic acid. MS (ESI+) [(M+H)+] 436.1.

Example 83

2-(3-Fluoro-5-morpholin-4-yl-phenyl)-4,4-dimethyl-1,2,3,4-tetrahydro-quinolin-6-yl]-[3-(1-hydroxy-1-methyl-ethyl)-pyrrolidin-1-yl]-methanone

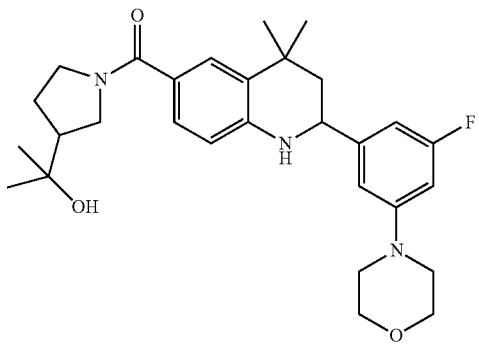 [SMILES: CC1(C)CC(c2cc(F)cc(N3CCOCC3)c2)Nc2ccc(C(=O)N3CCC(C(C)(C)O)C3)cc21]

The title compound was prepared in analogy to example 28 starting from 2-(3-fluoro-5-morpholin-4-yl-phenyl)-4,4-dimethyl-1,2,3,4-tetrahydro-quinoline-6-carboxylic acid. MS (ESI+) [(M+H)+] 496.2.

Example 84

2-(5-Fluoro-2-isopropoxy-phenyl)-4,4-dimethyl-1,2,3,4-tetrahydro-quinoline-6-carboxylic acid cyclobutylamide

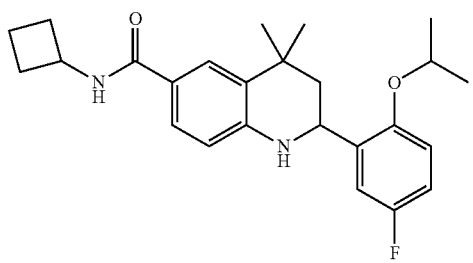 [SMILES: CC(C)Oc1ccc(F)cc1C1CC(C)(C)c2cc(C(=O)NC3CCC3)ccc2N1]

The title compound was prepared in analogy to example 28 starting from 2-(5-fluoro-2-isopropoxy-phenyl)-4,4-dimethyl-1,2,3,4-tetrahydro-quinoline-6-carboxylic acid. MS (ESI+) [(M+H)+] 411.2.

Example 85

2-(5-Fluoro-2-isopropoxy-phenyl)-4,4-dimethyl-1,2,3,4-tetrahydro-quinoline-6-carboxylic acid (2-hydroxy-1-hydroxymethyl-ethyl)-amide

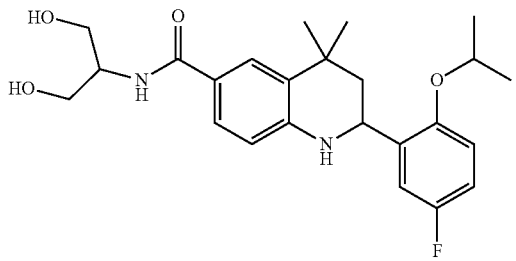 [SMILES: CC(C)Oc1ccc(F)cc1C1CC(C)(C)c2cc(C(=O)NC(CO)CO)ccc2N1]

The title compound was prepared in analogy to example 28 starting from 2-(5-fluoro-2-isopropoxy-phenyl)-4,4-dimethyl-1,2,3,4-tetrahydro-quinoline-6-carboxylic acid. MS (ESI+) [(M+H)+] 431.1.

Example 86

[2-(5-Fluoro-2-isopropoxy-phenyl)-4,4-dimethyl-1,2,3,4-tetrahydro-quinolin-6-yl]-(3-hydroxy-3-methyl-pyrrolidin-1-yl)-methanone

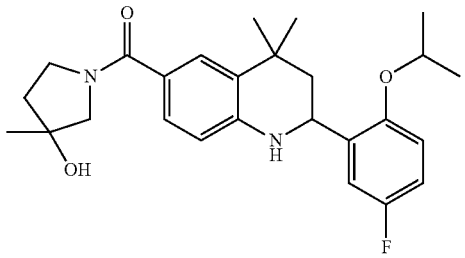 [SMILES: CC(C)Oc1ccc(F)cc1C1CC(C)(C)c2cc(C(=O)N3CCC(C)(O)C3)ccc2N1]

The title compound was prepared in analogy to example 28 starting from 2-(5-fluoro-2-isopropoxy-phenyl)-4,4-dimethyl-1,2,3,4-tetrahydro-quinoline-6-carboxylic acid. MS (ESI+) [(M+H)+] 441.3.

Example 87

2-(3-Chloro-4-fluoro-phenyl)-4,4-dimethyl-1,2,3,4-tetrahydro-quinoline-6-carboxylic acid (1-benzyl-piperidin-4-yl)-amide

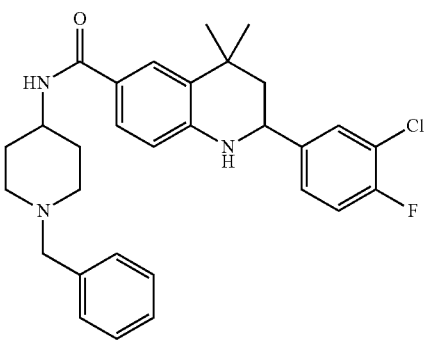 [SMILES: CC1(C)CC(c2ccc(F)c(Cl)c2)Nc2ccc(C(=O)NC3CCN(Cc4ccccc4)CC3)cc21]

The title compound was prepared in analogy to example 28 starting from 2-(3-chloro-4-fluoro-phenyl)-4,4-dimethyl-1,2,3,4-tetrahydro-quinoline-6-carboxylic acid. MS (ESI⁺) [(M+H)⁺] 506.2.

Example 88

2-(3-Fluoro-5-morpholin-4-yl-phenyl)-4,4-dimethyl-1,2,3,4-tetrahydro-quinoline-6-carboxylic acid (2-hydroxy-ethyl)-amide

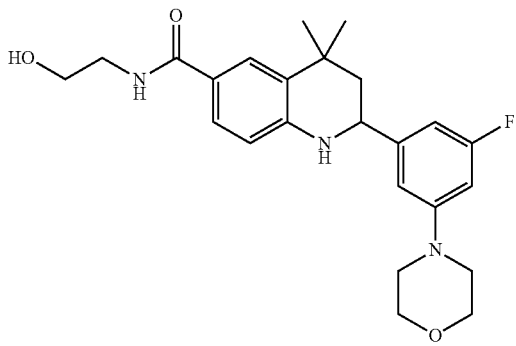 [SMILES: CC1(C)CC(c2cc(F)cc(N3CCOCC3)c2)Nc2ccc(C(=O)NCCO)cc21]

The title compound was prepared in analogy to example 28 starting from 2-(3-fluoro-5-morpholin-4-yl-phenyl)-4,4-dimethyl-1,2,3,4-tetrahydro-quinoline-6-carboxylic acid. MS (ESI⁺) [(M+H)⁺] 428.1.

Example 89

[4,4-Dimethyl-2-(3-morpholin-4-yl-phenyl)-1,2,3,4-tetrahydro-quinolin-6-yl]-[3-(1-hydroxy-1-methyl-ethyl)-pyrrolidin-1-yl]-methanone

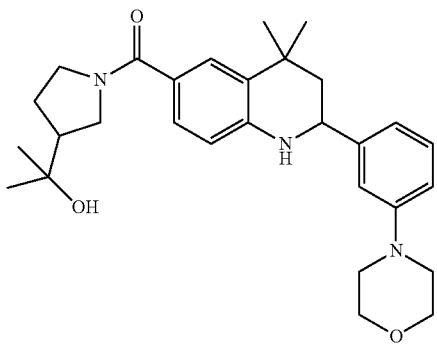 [SMILES: CC1(C)CC(c2cccc(N3CCOCC3)c2)Nc2ccc(C(=O)N3CCC(C(C)(C)O)C3)cc21]

The title compound was prepared in analogy to example 28 starting from 4,4-dimethyl-2-(3-morpholin-4-yl-phenyl)-1,2,3,4-tetrahydro-quinoline-6-carboxylic acid. MS (ESI⁺) [(M+H)⁺] 478.1.

Example 90

Scintillation Proximity Assay

Preparation of Enzymes

Recombinant human AMPK α1β1γ1, α2β1γ1 or AMPK α subunit truncations α1(1-335), α1(1-394) and α2(1-394) were constructed, expressed and purified as described previously (Pang, T., Zhang, Z. S., Gu, M., Qiu, B. Y., Yu, L. F., Cao, P. R., Shao, W., Su, M. B., Li, J. Y., Nan, F. J., and Li, J. (2008). Rat liver AMPK heterotrimer enzyme was obtained from Upstate (Billerica, Mass., U.S.A.).

Scintillation Proximity Assay

Before the Scintillation Proximity Assay (SPA) assay, 200 nM recombinant AMPK proteins (α1β1γ1, α2β1γ1, α1(1-335), α1(1-394) or α2(1-394)) were fully phosphorylated as described previously (Pang et al., 2008). SPA reactions were performed in 96-well plates at a final volume of 50 μL containing 20 mM Tris-HCl pH 7.5, 5 mM MgCl₂, 1 mM DTT, 2 μM biotin-SAMS, 2 μM ATP, 0.2 μCi/well [γ-³³P]ATP, and various amount of activator. Reactions were initiated by the addition of 50 nM recombinant AMPK proteins to the reaction solutions and incubated at 30° C. for 2 hours. After that, reactions were terminated by the addition of 40 μL stop solution containing 80 μg streptavidin-coated SPA beads per well, 50 mM EDTA, 0.1% Triton X-100 in PBS, pH 7.5 and incubated for 1 hour. Finally, a 160 μL suspension solution containing 2.4 M CsCl, 50 mM EDTA, and 0.1% Triton X-100 in PBS (pH 7.5) was added to the reaction solution to suspend SPA beads completely. SPA signals were determined with a Wallac MicroBeta plate counter (PerkinElmer) 30 min later for calculation of the amount of product formed. The amount of products formed in 2 hour was plotted against activator concentrations to determine the effective concentration of the activator (EC50) required for 50% of maximal enzyme activity.

Compounds as described above have EC50 values between 0.5 μM and 50 μM, preferred compounds have EC50 values between 0.5 μM and 10 μM, particularly preferred compounds have EC50 values between 0.5 μM and 1 μM.

Selected compounds of formula (I) have the following EC50, obtained by using the foregoing Scintillation Proximity Assay.

| Example No. | EC50 (μM) |
| --- | --- |
| Example 1 | 2.07 |
| Example 2 | 3.21 |
| Example 3 | 6.12 |
| Example 4 | 13.22 |
| Example 5 | 1.24 |
| Example 6 | 7.41 |
| Example 7 | 2.29 |
| Example 8 | 4.44 |
| Example 9 | 1.68 |
| Example 10 | 3.48 |
| Example 11 | 4.96 |
| Example 12 | 5.92 |
| Example 13 | 2.63 |
| Example 14 | 3.76 |
| Example 15 | 7.6 |
| Example 16 | 8.61 |
| Example 17 | 4.54 |
| Example 18 | 4.58 |
| Example 19 | 2.13 |
| Example 20 | 3.31 |
| Example 22 | 5.35 |
| Example 23 | 7.02 |
| Example 25 | 4.83 |
| Example 26 | 2.1 |
| Example 27 | 1.49 |
| Example 28 | 11.36 |
| Example 30 | 2.47 |
| Example 31 | 2.58 |
| Example 32 | 1.24 |
| Example 33 | 13.58 |
| Example 34 | 2.71 |
| Example 35 | 6.88 |
| Example 36 | 5.63 |
| Example 37 | 13.91 |
| Example 38 | 2.38 |
| Example 39 | 4.95 |
| Example 40 | 3.69 |
| Example 41 | 5.17 |

-continued

| Example No. | EC50 (μM) |
|---|---|
| Example 42 | 3.77 |
| Example 43 | 5.86 |
| Example 44 | 3.02 |
| Example 45 | 1.76 |
| Example 46 | 7.62 |
| Example 47 | 11.41 |
| Example 48 | 2.1 |
| Example 49 | 3.23 |
| Example 50 | 2.87 |
| Example 51 | 3.58 |
| Example 52 | 4.84 |
| Example 53 | 1.38 |
| Example 54 | 2.61 |
| Example 55 | 3.7 |
| Example 56 | 3.38 |
| Example 57 | 2.36 |
| Example 58 | 3.74 |
| Example 59 | 11.35 |
| Example 60 | 4.41 |
| Example 61 | 5.98 |
| Example 62 | 1.59 |
| Example 63 | 2.37 |
| Example 64 | 7.68 |
| Example 66 | 5.53 |
| Example 67 | 15.06 |
| Example 68 | 1.56 |
| Example 69 | 4.18 |
| Example 70 | 9.17 |

Example A

A compound of formula (I) can be used in a manner known per se as the active ingredient for the production of tablets of the following composition:

|  | Per tablet |
|---|---|
| Active ingredient | 200 mg |
| Microcrystalline cellulose | 155 mg |
| Corn starch | 25 mg |
| Talc | 25 mg |
| Hydroxypropylmethylcellulose | 20 mg |
| Total | 425 mg |

Example B

A compound of formula (I) can be used in a manner known per se as the active ingredient for the production of capsules of the following composition:

|  | Per capsule |
|---|---|
| Active ingredient | 100.0 mg |
| Corn starch | 20.0 mg |
| Lactose | 95.0 mg |
| Talc | 4.5 mg |
| Magnesium stearate | 0.5 mg |
| Total | 220.0 mg |

The invention claimed is:
1. A compound of formula (I)

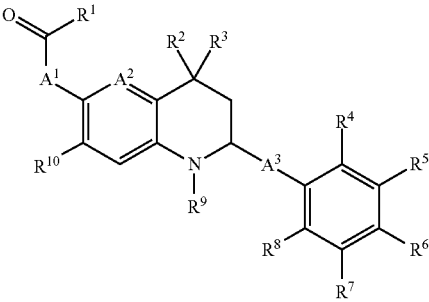

wherein
$A^1$ is absent or —$CH_2$—;
$A^2$ is nitrogen or —CH—;
$A^3$ is absent or —$C(CH_3)_2$—;
$R^1$ is hydroxyl or $NR^{11}R^{12}$;
$R^2$ and $R^3$ are each independently selected from the group consisting of alkyl, alkenyl and phenyl;
or $R^2$ and $R^3$ together with the carbon atom to which they are attached form cycloalkyl;
$R^4$, $R^5$, $R^6$, $R^7$ and $R^8$ are each independently selected from the group consisting of hydrogen, alkyl, alkoxy, halogen, alkylsulfonyl, morpholinyl, piperazinyl and alkylpiperazinyl;
$R^9$ is selected from the group consisting of hydrogen, alkyl, benzyl and alkylaminocarbonyl;
$R^{10}$ is hydrogen or halogen; and
$R^{11}$ and $R^{12}$ are each independently selected from the group consisting of hydrogen, alkyl, cycloalkyl, hydroxyalkyl, oxetanyl, alkylpiperidinyl, 1,1-dioxothiomorpholinylalkyl and benzylpiperidinyl;
or $R^{11}$ and $R^{12}$ together with the nitrogen atom to which they are attached form morpholinyl, piperazinyl, alkylpiperazinyl, alkylsulfonylpiperazinyl, alkylhydroxypyrrolidinyl or hydroxyalkylpyrrolidinyl;
or a pharmaceutically acceptable salt or ester thereof.

2. A compound according to claim 1, wherein $R^2$ and $R^3$ are each independently selected from the group consisting of methyl, ethyl, ethenyl and phenyl, or $R^2$ and $R^3$ together with the carbon atom to which they are attached form cyclopropyl, cyclopentyl or cyclohexyl.

3. A compound according to claim 1, wherein $R^4$ is selected from the group consisting of hydrogen, alkyl, alkoxy, halogen or alkylsulfonyl.

4. A compound according to claim 1, wherein $R^4$ is selected from the group consisting of hydrogen, methyl, fluoro, chloro, bromo and methylsulfonyl.

5. A compound according to claim 1, wherein $R^5$ is selected from the group consisting of hydrogen, alkyl, alkoxy, halogen, alkylsulfonyl, morpholinyl, piperazinyl and alkylpiperazinyl.

6. A compound according to claim 1, wherein $R^5$ is selected from the group consisting of hydrogen, chloro, and morpholinyl.

7. A compound according to claim 1, wherein $R^6$ is hydrogen or halogen.

8. A compound according to claim 1, wherein $R^6$ is hydrogen or fluoro.

9. A compound according to claim 1, wherein $R^7$ is selected from the group consisting of hydrogen, halogen, alkylsulfonyl and morpholinyl.

10. A compound according to claim 1, wherein $R^7$ is selected from the group consisting of hydrogen, fluoro, chloro, bromo and methylsulfonyl.

11. A compound according to claim 1, wherein $R^8$ is hydrogen or alkyl.

12. A compound according to claim 1, wherein $R^8$ is hydrogen or methyl.

13. A compound according to claim 1, wherein $R^9$ is selected from the group consisting of hydrogen, pentyl, dimethylaminocarbonyl and benzyl.

14. A compound according to claim 1, wherein $R^{10}$ is hydrogen or chloro.

15. A compound according to claim 1, wherein $R^{11}$ and $R^{12}$ are each independently selected from the group consisting of hydrogen, alkyl, cycloalkyl, hydroxyalkyl and alkylpiperidinyl, or $R^{11}$ and $R^{12}$ together with the nitrogen atom to which they are attached form morpholinyl, piperazinyl, alkylpiperazinyl or alkylsulfonylpiperazinyl.

16. A compound according to claim 1, wherein $R^{11}$ and $R^{12}$ are each independently selected from the group consisting of hydrogen, methyl, propyl, dihydroxybutyl, cyclopropyl, cyclobutyl, methylpiperidinyl and hydroxyethyl or $R^{11}$ and $R^{12}$ together with the nitrogen atom to which they are attached form morpholinyl, piperazinyl, methylpiperazinyl or methylsulfonylpiperazinyl.

17. A pharmaceutical composition comprising a compound according to claim 1 and a therapeutically inert carrier.

* * * * *